United States Patent
Tanaka et al.

(10) Patent No.: US 9,268,225 B2
(45) Date of Patent: Feb. 23, 2016

(54) COMPOSITION, RESIST PATTERN-FORMING METHOD, COMPOUND, METHOD FOR PRODUCTION OF COMPOUND, AND POLYMER

(71) Applicant: JSR CORPORATION, Tokyo (JP)

(72) Inventors: Kiyoshi Tanaka, Tokyo (JP); Shinya Minegishi, Tokyo (JP); Kazunori Kusabiraki, Tokyo (JP); Takahiro Hayama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/273,608

(22) Filed: May 9, 2014

(65) Prior Publication Data

US 2014/0248563 A1    Sep. 4, 2014

Related U.S. Application Data

(63) Continuation of application No. PCT/JP2012/079041, filed on Nov. 8, 2012.

(30) Foreign Application Priority Data

Nov. 11, 2011 (JP) ................. 2011-247983

(51) Int. Cl.
| | | |
|---|---|---|
| *G03F 7/11* | (2006.01) | |
| *G03F 7/038* | (2006.01) | |
| *C08F 220/26* | (2006.01) | |
| *C07C 69/734* | (2006.01) | |
| *G03F 7/20* | (2006.01) | |
| *C08F 220/22* | (2006.01) | |
| *G03F 7/004* | (2006.01) | |
| *G03F 7/039* | (2006.01) | |

(52) U.S. Cl.
CPC ............ *G03F 7/0388* (2013.01); *C07C 69/734* (2013.01); *C08F 220/22* (2013.01); *C08F 220/26* (2013.01); *G03F 7/0046* (2013.01); *G03F 7/038* (2013.01); *G03F 7/11* (2013.01); *G03F 7/2041* (2013.01); *C07C 2101/14* (2013.01); *G03F 7/0397* (2013.01)

(58) Field of Classification Search
CPC ..... G03F 7/0046; G03F 7/038; G03F 7/0388; G03F 7/0397; G03F 7/2041; G03F 7/11; C08F 220/22; C08F 220/26
USPC .............. 430/270.1, 271.1; 526/320; 524/378
See application file for complete search history.

(56) References Cited

U.S. PATENT DOCUMENTS

| | | | |
|---|---|---|---|
| 4,910,122 A | | 3/1990 | Arnold et al. |
| 8,568,886 B2 * | 10/2013 | Matsuda et al. ............. 428/421 |
| 2013/0065182 A1* | 3/2013 | Mori et al. ................. 430/285.1 |
| 2014/0093024 A1* | 4/2014 | Park .............................. 375/362 |

FOREIGN PATENT DOCUMENTS

| | | |
|---|---|---|
| EP | 358182 A2 * | 3/1990 |
| JP | 06-012452 B2 | 5/1984 |
| JP | 05-222128 | 8/1993 |
| JP | H06-110199 A | 4/1994 |
| JP | 2002-155112 | 5/2002 |
| JP | 2002-220420 | 8/2002 |
| JP | 2004053822 A * | 2/2004 |
| JP | 2005-107476 | 4/2005 |
| JP | 2006-91798 | 4/2006 |
| JP | 2006-171440 | 6/2006 |
| JP | 2006145775 A * | 6/2006 |
| JP | 2006-194962 | 7/2006 |
| JP | 2007-140228 | 6/2007 |
| JP | 2007-178621 A | 7/2007 |
| JP | 2010-107793 | 5/2010 |
| JP | 2010-204634 | 9/2010 |
| JP | 2011-016746 | 1/2011 |
| JP | 2011-221513 | 11/2011 |
| WO | WO 2008/047678 | 4/2008 |
| WO | WO 2009/041270 | 4/2009 |

OTHER PUBLICATIONS

International Search Report for corresponding International Application No. PCT/JP2012/079041, Jan. 15, 2013.
Office Action issued Oct. 27, 2015, in Japanese Patent Application No. 2012-218885 (w/ English translation).

* cited by examiner

*Primary Examiner* — Amanda C Walke
(74) *Attorney, Agent, or Firm* — Oblon, McClelland, Maier & Neustadt, L.L.P.

(57) ABSTRACT

A composition includes a polymer component including a first polymer having a first structural unit represented by a following formula (1), and a solvent. In the formula (1), $R^1$ represents a hydrogen atom or a monovalent organic group having 1 to 20 carbon atoms. $R^2$ represents a single bond or a divalent organic group having 1 to 20 carbon atoms. $R^3$ represents a hydrogen atom or a monovalent organic group having 1 to 20 carbon atoms. $R^Q$ represents a perfluoroalkyl group having 1 to 5 carbon atoms. $R^X$ represents a hydrogen atom or a monovalent base-labile group.

(1)

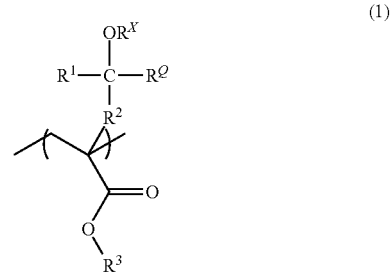

19 Claims, No Drawings

COMPOSITION, RESIST PATTERN-FORMING METHOD, COMPOUND, METHOD FOR PRODUCTION OF COMPOUND, AND POLYMER

CROSS-REFERENCE TO RELATED APPLICATIONS

The present application is a continuation application of International Application No. PCT/JP2012/079041, filed Nov. 8, 2012, which claims priority to Japanese Patent Application No. 2011-247983, filed Nov. 11, 2011. The contents of these applications are incorporated herein by reference in their entirety.

BACKGROUND OF THE INVENTION

1. Field of the Invention

The present invention relates to a composition, a resist pattern-forming method, a compound, a method for production of the compound and a polymer.

2. Discussion of the Background

In the field of microfabrication typified by production of integrated circuit devices, chemically amplified resists have been conventionally used. In the chemically amplified resists, irradiation with, for example, a radioactive ray having a short wavelength such as an excimer laser beam generates an acid at light-exposed sites to cause a difference in rates of dissolution in an alkaline developer solution between light-exposed sites and light-unexposed sites by a reaction by way of the acid as a catalyst, thereby forming a resist pattern on a substrate.

In such chemically amplified resists, as a method for forming a finer resist pattern, utilization of a liquid immersion lithography process (liquid immersion lithography) is expanding in which exposure is conducted while allowing a space between a lens and a resist film to be filled with a liquid immersion media such as, for example, pure water or a fluorine-based inert liquid. The liquid immersion lithography process allows for an increase in numerical aperture (NA) of the lens, and further provides advantages that a depth of focus is hardly decreased and additionally a high resolution can be achieved even under increased NAs, and the like.

On the other hand, in the resist pattern formation by the liquid immersion lithography process, it is required to improve a scan speed, while inhibiting pattern defects attributed to elution of a component from the resist film and/or beads of a liquid remaining on the surface of the resist film. As a technique for meeting the requirements, it is proposed to provide an upper layer film for liquid immersion lithography between the resist film and a liquid immersion medium (see, Japanese Unexamined Patent Application, Publication No. 2006-91798 and PCT International Publication Nos. WO 2008/47678 and WO 2009/41270). These Patent Documents disclose that: the upper layer film for liquid immersion lithography is provided on the resist film using a water-insoluble and alkali-soluble polymer; during the liquid immersion lithography, inhibition of the elution of the resist film component and the like is achieved based on water repellency exhibited by the upper layer film for liquid immersion lithography; and additionally, in a subsequent step of development, the upper layer film for liquid immersion lithography is peeled from the surface of the resist film by dissolving the upper layer film for liquid immersion lithography in a developer solution.

In addition, recently, lithography in which an EUV, an electron beam or the like (hereinafter, may be also referred to as "EUV and the like") having a shorter wavelength than the excimer laser beam is used has been investigated as another method for forming a finer pattern (see Japanese Unexamined Patent Application, Publication Nos. 2006-171440, 2011-16746 and 2010-204634). However, in the case of the lithography carried out using the EUV is the like, an exposure needs to be carried out under vacuum, and therefore a reduction of outgassing from the resist film is demanded. Accordingly, as a technique for meeting the demand, it has been proposed to provide an upper layer film for EUV and the like that covers the surface of the resist film. Also in the upper layer film of this type, suppression of outgassing or the like during, for example, an exposure to the EUV and the like is expected to be enhanced by the water repellency exhibited by the upper layer film; however, the upper layer film needs to be peeled from the surface of the resist film in a subsequent development step by dissolving the upper layer film in a developer solution.

SUMMARY OF THE INVENTION

According to one aspect of the present invention, a composition includes a polymer component including a first polymer having a first structural unit represented by a formula (1), and a solvent.

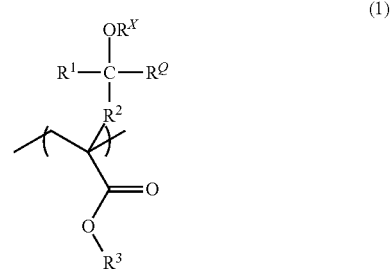

In the formula (1), $R^1$ represents a hydrogen atom or a monovalent organic group having 1 to 20 carbon atoms; $R^2$ represents a single bond or a divalent organic group having 1 to 20 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

According to another aspect of the present invention, a resist pattern-forming method includes providing a resist film using a photoresist composition. A resist upper layer film is provided on the resist film using the composition. The resist film having the resist upper layer film provided on the resist film is exposed. The exposed resist film is developed.

According to further aspect of the present invention, a compound is represented by a formula (i).

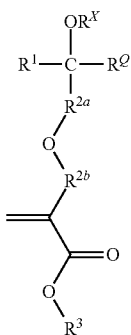

(i)

In the formula (i), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

According to further aspect of the present invention, a method for producing a compound, includes reacting a dihydroxy compound represented by a formula (i-a) with a haloalkylacrylic acid ester compound represented by a formula (i-b) to produce a compound represented by formula (i').

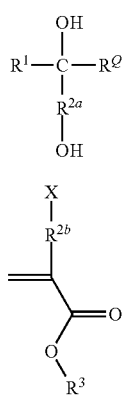

(i-a)

(i-b)

(i')

In the formulae (i-a), (i-b) and (i'), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and X represents a halogen atom.

According to further aspect of the present invention, a polymer includes a structural unit represented by a formula (1A).

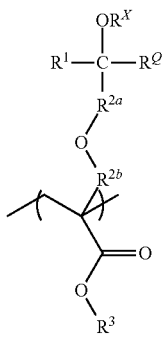

(1A)

In the formula (1A), R' represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

DESCRIPTION OF THE EMBODIMENTS

According to an embodiment of the present invention made for solving the aforementioned problems, a composition is provided, containing:

a polymer component (hereinafter, may be also referred to as "polymer component (A)") including a polymer having a structural unit (I) represented by the following formula (1) (hereinafter, may be also referred to as "polymer (a)"); and a solvent (hereinafter, may be also referred to as "solvent (B)"),

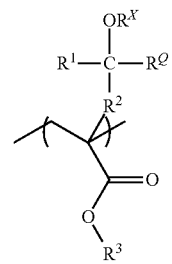

(1)

wherein in the formula (1), $R^1$ represents a hydrogen atom or a monovalent organic group having 1 to 20 carbon atoms; $R^2$ represents a single bond or a divalent organic group having 1 to 20 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

The composition according to the embodiment of the present invention contains, as the polymer component (A), the polymer (a) having a structural unit (I) that includes a group represented by —$CR^1R^Q(OR^X)$ (hereinafter, may be also referred to as "specific group (x)"). According to the composition, when the polymer (a) has, in addition to —$COOR^3$ group, the specific group (x) at a position away from the polymer chain through $R^2$, a resist upper layer film provided can exhibit superior water repellency, and occurrence of defects such as bridge defects and blob defects in a resist pattern can be inhibited.

The solvent (B) preferably contains an ether solvent. The polymer (a) is soluble in the solvent (B) containing the ether solvent due to the specific group (x) included in the structural unit (I). Therefore, when the solvent (B) contains the ether solvent, the viscosity of the composition for forming a resist upper layer film can be lowered, resulting in a reduction of the amount of the composition coated and a cost reduction. Moreover, it is preferred that the solvent (B) further contains an alcohol solvent.

The divalent organic group having 1 to 20 carbon atoms which may be represented by $R^2$ in the above formula (1) is preferably a divalent linear hydrocarbon group having 1 to 20 carbon atoms, a divalent alicyclic hydrocarbon group having 3 to 20 carbon atoms, or a group obtained by combining —O— with at least one of these groups. According to the composition, when $R^2$ represents the specific group, the aforementioned effects can be enhanced.

The monovalent organic group which may be represented by $R^1$ and $R^3$ in the above formula (1) is preferably a monovalent hydrocarbon group, a monovalent hetero atom-containing group that includes between adjacent two carbon atoms of the same —O—, —CO—, —COO—, —NHCO—, —NH—SO$_2$—, —S— or a combination thereof, or a monovalent group derived from the hydrocarbon group and the hetero atom-containing group by substituting a part or all of included hydrogen atoms with a fluorine atom, a hydroxy group, a carboxy group, an amino group, a cyano group or a combination thereof. According to the composition, when $R^1$ and $R^3$ represent the specific group, the aforementioned effects can be enhanced.

It is preferred that the polymer component (A) further has, in a polymer which is identical to or different from the polymer (a), i.e., in the polymer (a) or other polymer which is different from the polymer (a), the structural unit (II) represented by the following formula (2),

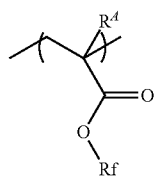

(2)

wherein in the formula (2), $R^A$ represents a hydrogen atom, a methyl group, a fluorine atom or a trifluoromethyl group; and Rf represents a fluorinated hydrocarbon group having 1 to 20 carbon atoms.

When the polymer component (A) thus further has the structural unit (II), water repellency of the resist upper layer film provided from the composition can be enhanced through the synergic effects between the structural unit (II) and the specific group (x) included in the structural unit (I).

It is preferred that the polymer component (A) further has, in a polymer which is identical to or different from the polymer (a), a structural unit (III) that is a structural unit that includes a group represented by the following formula (3a), a structural unit that is other than the structural unit (I) and that includes a group represented by the following formula (3b), or a combination thereof,

(3a)

(3b)

wherein in the formula (3a), $R^N$ represents a fluorinated hydrocarbon group having 1 to 20 carbon atoms, and in the formula (3b), $R^a$ represents a monovalent organic group having 1 to 20 carbon atoms; and $R^q$ represents a perfluoroalkyl group having 1 to 5 carbon atoms.

According to the composition, when the polymer component (A) further has the structural unit (III), removability of the resist upper layer film provided can be improved.

It is preferred that the polymer component (A) preferably includes, in a polymer which is identical to or different from the polymer (a), a structural unit (IV) that includes a sulfo group. According to the composition, when the polymer component (A) further has the structural unit (IV), removability and peel resistance of the resist upper layer film provided can be improved.

It is preferred that the polymer component (A) further has, in a polymer which is identical to or different from the polymer (a), a structural unit (V) that is a structural unit that includes a carboxy group, a structural unit that includes a group represented by the following formula (v), or a combination thereof,

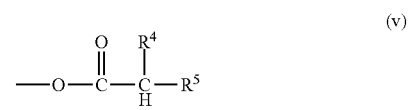

(v)

wherein in the formula (v), $R^4$ represents a hydrogen atom, a halogen atom, a nitro group, an alkyl group, a monovalent alicyclic hydrocarbon group, an alkoxy group, an acyl group, an aralkyl group or an aryl group, wherein a part or all of hydrogen atoms included in the alkyl group, the alicyclic hydrocarbon group, the alkoxy group, the acyl group, the aralkyl group and the aryl group which are represented by $R^4$ are unsubstituted or substituted; $R^5$ represents —C(=O)—$R^6$, —S(=O)$_2$—$R^7$, —$R^8$—CN or —$R^9$—NO$_2$; $R^6$ and $R^7$ each independently represent a hydrogen atom, an alkyl group, a fluorinated alkyl group, a monovalent alicyclic hydrocarbon group, an alkoxy group, a cyano group, a cyanomethyl group, an aralkyl group or an aryl group, or $R^4$ and one of $R^6$ and $R^7$ taken together represent a ring structure, and the rest of $R^6$ and $R^7$ represents a hydrogen atom, an alkyl group, a fluorinated alkyl group, a monovalent alicyclic hydrocarbon group, an alkoxy group, a cyano group, a cyanomethyl group, an aralkyl group or an aryl group; and $R^8$ and $R^9$ each independently represent a single bond, a methylene group or an alkylene group having 2 to 5 carbon atoms.

According to the composition, when the polymer component (A) further has the structural unit (V), the removability and the peel resistance of the resist upper layer film provided can be improved.

According to another embodiment of the present invention, a resist pattern-forming method is provided, including:

providing a resist film using a photoresist composition (hereinafter, may be also referred to as "step (1)");

providing a resist upper layer film on the resist film (hereinafter, may be also referred to as "step (2)");

exposing the resist film having the resist upper layer film provided thereon (hereinafter, may be also referred to as "step (3)"); and developing the exposed resist film (hereinafter, may be also referred to as "step (4)"), wherein the composition according to the embodiment of the present invention is used in providing the resist upper layer film.

According to the resist pattern-forming method, a resist upper layer film exhibiting superior water repellency can be provided, and occurrence of defects such as bridge defects and blob defects in a resist pattern can be inhibited as a result of the use of the aforementioned composition.

An exposure in the exposure step is preferably carried out through a liquid immersion medium. The resist pattern-forming method according to the embodiment of the present invention enables a resist upper layer film exhibiting superior water repellency to be provided, and therefore can be particularly suitably used for an exposure though a liquid immersion medium.

An exposure light in the exposure step is preferably a far ultraviolet ray, an EUV or an electron beam. The resist pattern-forming method can be particularly suitably used for a process in which a far ultraviolet ray is used as an exposure light such as liquid immersion lithography, or alternatively, a process in which an EUV or an electron beam is used as an exposure light, the latter process requiring inhibition of outgassing from a resist film, since the resist pattern-forming method can provide a resist upper layer film exhibiting superior water repellency.

According to still another embodiment of the present invention, a compound represented by the following formula (i) is provided,

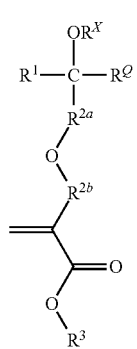

wherein in the formula (i), $R^1$ represents a hydrogen atom or a monovalent organic group having 1 to 20 carbon atoms;

$R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

The compound (hereinafter, may be also referred to as "compound (i)") can be suitably used as, for example, a monomer that gives a polymer constituting the composition, as a result of having the specific structure.

A method for producing a compound represented by the following formula (i') according to yet still another embodiment of the present invention includes:

reacting a dihydroxy compound represented by the following formula (i-a) with a haloalkylacrylic acid ester compound represented by the following formula (i-b),

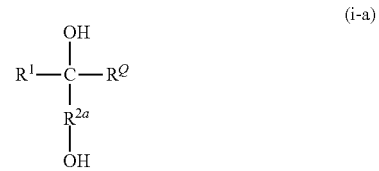

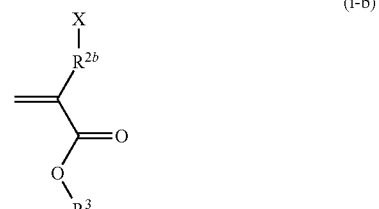

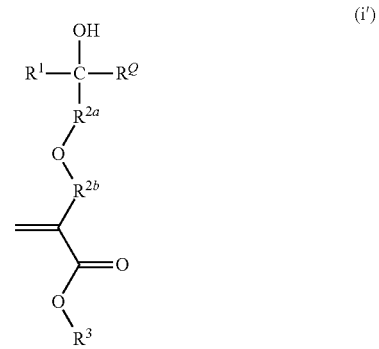

wherein in the formulae (i-a), (i-b) and (i'), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and X represents a halogen atom.

According to the method for production, the compound represented by the above formula (i') can be produced conveniently and in high yield.

According to even yet still another embodiment of the present invention, a polymer has a structural unit (I-A) represented by the following formula (1A),

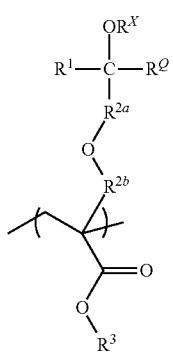

(1A)

wherein in the formula (1A), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

Since the polymer has the specific structural unit, the polymer can be suitably used as, for example, the polymer component constituting the composition according to the embodiment of the present invention.

In the present specification, the term "organic group" as referred to means a group having at least one carbon atom.

As explained in the foregoing, in the composition and the resist pattern-forming method according to the embodiments of the present invention, when the polymer having a structural unit that includes the specific structure is involved, a resist upper layer film exhibiting superior water repellency can be provided, and occurrence of defects such as bridge defects and blob defects in a resist pattern can be inhibited. Moreover, the compound according to the embodiment of the present invention can be suitably used as a monomer that gives a polymer constituting the composition; according to the method for production of the compound according to the embodiment of the present invention, the compound can be produced conveniently and in high yield. The polymer according to the embodiment of the present invention can be suitably used as the polymer component of the composition. The composition can be suitably used for providing a resist upper layer film, and additionally can also be used for other intended usages such as provision of a resist film. The embodiments will now be described in detail.

Composition for Forming Resist Upper Layer Film

A composition for forming a resist upper layer film according to an embodiment of the present invention contains (A) a polymer component and (B) a solvent. Moreover, the composition for forming a resist upper layer film may also include an optional component within a range not leading to impairment of the effects of the present invention. Hereinafter, each component will be explained.

(A) Polymer Component

The polymer component (A) includes a polymer (a) having the structural unit (I) represented by the above formula (1). The polymer component (A) may be constituted with only the polymer (a), or may include, in addition to the polymer (a), a polymer (b) that does not have the structural unit (I). The polymer component (A) may include one, or two or more types of the polymers.

The polymer component (A) may further have, in addition to the structural unit (I), a structural unit (II) represented by the above formula (2); a structural unit (III) that is a structural unit that includes a group represented by the above formula (3a), a structural unit that is other than the structural unit (I) and that includes a group represented by the above formula (3b), or a combination thereof; a structural unit (IV) that includes a sulfo group; a structural unit (V) that is a structural unit that includes a carboxy group, a structural unit that includes a group represented by the above formula (v), or a combination thereof; and the like, in the polymer (a). Moreover, examples of the polymer (b) that may be included in the polymer component (A) include a polymer having the structural units (II) to (V) and the like. Hereinafter, each structural unit will be explained.

Structural Unit (I)

The structural unit (I) is a structural unit represented by the above formula (1). When the polymer component (A) has the structural unit (I), and in addition to —COOR$^3$ group, the specific group (x) at a specific position away from the polymer chain through $R^2$, the composition for forming a resist upper layer film enables a resist upper layer film exhibiting superior water repellency to be provided and occurrence of defects such as bridge defects and blob defects in a resist pattern to be inhibited.

In the above formula (1), $R^1$ represents a hydrogen atom or a monovalent organic group having 1 to 20 carbon atoms; $R^2$ represents a single bond or a divalent organic group having 1 to 20 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

Examples of the monovalent organic group having 1 to 20 carbon atoms which may be represented by $R^1$ and $R^3$ include a hydrocarbon group having 1 to 20 carbon atoms, a monovalent hetero atom-containing group that includes between adjacent two carbon atoms of the same a group having a hetero atom, a monovalent group derived from the hydrocarbon group and the hetero atom-containing group by substituting a part or all of included hydrogen atoms with a substituent, and the like. The monovalent organic group may include at least one of the group having a hetero atom and the substituent, respectively.

Examples of the hydrocarbon group having 1 to 20 carbon atoms include a monovalent linear hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the linear hydrocarbon group having 1 to 20 carbon atoms include:

an alkyl group such as a methyl group, an ethyl group, a propyl group, a butyl group and a pentyl group;

an alkenyl group such as an ethenyl group, a propenyl group, a butenyl group and a pentenyl group;

an alkynyl group such as an ethynyl group, a propynyl group, a butynyl group and a pentynyl group; and the like.

Examples of the alicyclic hydrocarbon group having 3 to 20 carbon atoms include:

a cycloalkyl group such as a cyclopropyl group, a cyclobutyl group, a cyclopentyl group, a cyclohexyl group, a cycloheptyl group, a cyclooctyl group, a norbornyl group and an adamantyl group;

a cycloalkenyl group such as a cyclopropenyl group, a cyclobutenyl group, a cyclopentenyl group, a cyclohexenyl group and a norbornenyl group; and the like.

Examples of the aromatic hydrocarbon group having 6 to 20 carbon atoms include:

an aryl group such as a phenyl group, a tolyl group, a xylyl group, a mesityl group, a naphthyl group and an anthryl group;

an aralkyl group such as a benzyl group, a phenethyl group, a naphthylmethyl group and an anthrylmethyl group; and the like.

Examples of the group having a hetero atom include —O—, —CO—, —COO—, —S—, —CS—, —OCS—, —SCO—, —SCS—, —NH—, —CONH—, —CSNH—, and the like. Among these, —O—, —CO—, —COO—, —NHCO—, —NH—SO$_2$— and —S— are preferred.

Examples of the substituent include: a halogen atom such as a fluorine atom, a chlorine atom, a bromine atom and an iodine atom; a hydroxy group; a carboxy group; an amino group; a cyano group; a nitro group; and the like. Among these, a fluorine atom, a hydroxy group, a carboxy group, an amino group and a cyano group are preferred.

$R^1$ represents preferably a hydrogen atom, a monovalent linear hydrocarbon group, a monovalent alicyclic hydrocarbon group, a monovalent fluorinated linear hydrocarbon group and a monovalent fluorinated alicyclic hydrocarbon group, more preferably a hydrogen atom and a monovalent perfluoroalkyl group, still more preferably a hydrogen atom and a trifluoromethyl group, and particularly preferably a trifluoromethyl group in light of more superior water repellency and superior inhibitory effect on occurrence of defects of the resist upper layer film provided from the composition for forming a resist upper layer film.

$R^3$ represents preferably a hydrogen atom, a monovalent linear hydrocarbon group, a monovalent alicyclic hydrocarbon group, a monovalent fluorinated linear hydrocarbon group and a monovalent fluorinated alicyclic hydrocarbon group, and more preferably a methyl group, an ethyl group, a butyl group, a cyclohexyl group and a hexafluoro-2-propyl group in light of more superior water repellency and superior inhibitory effect on occurrence of defects of the resist upper layer film provided from the composition for forming a resist upper layer film. $R^3$ may be a hetero atom-containing group for the purpose of adjusting solubility of the resist upper layer film provided from the composition for forming a resist upper layer film in a developer solution.

Examples of the divalent organic group having 1 to 20 carbon atoms which may be represented by $R^2$ include a divalent hydrocarbon group having 1 to 20 carbon atoms, a hetero atom-containing group that includes between adjacent two carbon atoms of the same a group having a hetero atom, a group derived from the hydrocarbon group and the hetero atom-containing group by substituting a part or all of included hydrogen atoms with a substituent, and the like.

Examples of the divalent hydrocarbon group having 1 to 20 carbon atoms include a divalent linear hydrocarbon group having 1 to 20 carbon atoms, a divalent alicyclic hydrocarbon group having 3 to 20 carbon atoms, a divalent aromatic hydrocarbon group having 6 to 20 carbon atoms, and the like.

Examples of the divalent linear hydrocarbon group having 1 to 20 carbon atoms include a methanediyl group, an ethanediyl group, a propanediyl group, a butanediyl group, a pentanediyl group, a hexanediyl group, an octanediyl group, a decanediyl group, a dodecanediyl group, a tetradecanediyl group, a hexadecanediyl group, an octadecanediyl group, an icosanediyl group, and the like.

Examples of the divalent alicyclic hydrocarbon group having 3 to 20 carbon atoms include a cyclopropanediyl group, a cyclobutanediyl group, a cyclopentanediyl group, a cyclohexanediyl group, a cyclooctanediyl group, a cyclodecanediyl group, and the like.

Examples of the divalent aromatic hydrocarbon group having 6 to 20 carbon atoms include a benzenediyl group, a toluenediyl group, a xylenediyl group, a naphthalenediyl group, an anthracenediyl group, a phenanthrenediyl group, a benzenediylmethanediyl group, a benzenediylethanediyl group, and the like.

Examples of the group having a hetero atom include the same groups as those exemplified as the group having a hetero atom that may be included in the monovalent organic group which may be represented by $R^1$ and $R^3$, and the like. Among these, —O—, —CO—, —COO—, —NHCO—, —NH—SO$_2$— and —S— are preferred, and —O— is more preferred.

Examples of the substituent include the same groups as those exemplified as the substituent that may be included in the monovalent organic group which may be represented by $R^1$ and $R^3$, and the like.

$R^2$ preferably represents a group obtained by combining —O— with at least one of the linear hydrocarbon group or the alicyclic hydrocarbon group.

Examples of the group obtained by combining —O— with at least one of the linear hydrocarbon group or the alicyclic hydrocarbon group include an alkanediyloxy group such as a methanediyloxy group, an ethanediyloxy group, a propanediyloxy group, a butanediyloxy group, a pentanediyloxy group, a hexanediyloxy group and an octanediyloxy group; a group having one —O— unit such as a methanediyloxymethanediyl group, a methanediyloxyethanediyl group, a methanediyloxy(1,2-propanediyl) group, a methanediyloxybutanediyl group and a methanediyloxycyclohexanediyl group; a group having two or more —O— units such as a propanediyloxyethanediyloxyethanediyl group; and the like.

Among these, $R^2$ represents preferably a divalent linear hydrocarbon group and a group having one —O— unit, more preferably a divalent linear hydrocarbon group having 1 to 4 carbon atoms or a group having one —O— unit and 1 to 4 carbon atoms, still more preferably a divalent linear hydrocarbon group having 2 or 3 carbon atoms or a group having one —O— unit and 2 or 3 carbon atoms, particularly preferably an ethanediyl group, a methanediyloxyethanediyl group and a methanediyloxy(1,2-propanediyl) group, and further particularly preferably a methanediyloxyethanediyl group and a methanediyloxy(1,2-propanediyl) group in light of more superior water repellency and superior inhibitory effect on occurrence of defects of the resist upper layer film provided from the composition for forming a resist upper layer film.

Examples of the perfluoroalkyl group having 1 to 5 carbon atoms which may be represented by $R^Q$ include a trifluoromethyl group, a pentafluoroethyl group, a heptafluoro-n-propyl group, a heptafluoro-i-propyl group, a nonafluoro-n-butyl group, a nonafluoro-i-butyl group, a nonafluoro-t-butyl group, a perfluoro-n-pentyl group, a perfluoro-n-pentyl group, a perfluoro-i-pentyl group, a perfluoro-neo-pentyl group, and the like. Among these, a trifluoromethyl group is preferred.

Examples of —CR$^1$R$^Q$(OR$^X$) in the above formula (1) wherein R$^X$ represents a hydrogen atom include a 2-hydroxy-1,1,1,3,3,3-hexafluoro-2-propyl group, a 1-hydroxy-2,2,2-trifluoroethyl group, a 2-hydroxy-1,1,1,4,4,4-hexafluoro-2-butyl group, a 2-hydroxy-1,1,1,3,3,4,4,4-octafluoro-2-butyl group, and the like. Among these, a 2-hydroxy-1,1,1,3,3,3-hexafluoro-2-propyl group and a 1-hydroxy-2,2,2-trifluoroethyl group are preferred, and a 2-hydroxy-1,1,1,3,3,3-hexafluoro-2-propyl group is more preferred.

The term "base-labile group" in the monovalent base-labile group which may be represented by $R^X$ as referred to means, for example, a group that substitutes a hydrogen atom of a hydroxy group and is dissociated in the presence of an alkali (for example, in a 2.38% by mass aqueous tetramethylammonium hydroxide (TMAH) solution at 23° C.). In a case where $R^X$ represents the base-labile group, the structural unit (I) has more superior water repellency, and therefore the proportion of the structural unit (I) introduced into the polymer (A) may be increased. As a result, solubility of the polymer (A) in an alkaline developer solution is increased through the action of the alkaline developer solution, and therefore it is expected that the occurrence of the defects such as the bridge defects or the blob defects is further inhibited. The monovalent base-labile group which may be represented by $R^X$ is preferably a group represented by the following formula (Ba-1) or a group represented by the following formula (Ba-2).

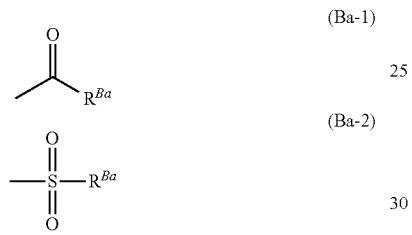

In the above formulae (Ba-1) and (Ba-2), $R^{Ba}$ each independently represent a monovalent hydrocarbon group having 1 to 20 carbon atoms. A part or all of hydrogen atoms included in the hydrocarbon group which are represented by $R^{Ba}$ are unsubstituted or substituted.

Examples of the monovalent hydrocarbon group having 1 to 20 carbon atoms which may be represented by $R^{Ba}$ include a monovalent linear hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent linear hydrocarbon group having 1 to 20 carbon atoms, the monovalent alicyclic hydrocarbon group having 3 to 20 carbon atoms and the monovalent aromatic hydrocarbon group having 6 to 20 carbon atoms include the same groups as the monovalent linear hydrocarbon group having 1 to 20 carbon atoms, the monovalent alicyclic hydrocarbon group having 3 to 20 carbon atoms and the monovalent aromatic hydrocarbon group having 6 to 20 carbon atoms exemplified as $R^1$, and the like.

Examples of the substituent of the monovalent hydrocarbon group which may be represented by $R^{Ba}$ include a fluorine atom, a hydroxy group, an amino group, a mercapto group, a carboxy group, a cyano group, an alkoxy group, an acyl group, an acyloxy group, and the like.

$R^{Ba}$ represents preferably a monovalent linear hydrocarbon group, more preferably a monovalent linear hydrocarbon group having 1 to 5 carbon atoms, and still more preferably a methyl group.

Examples of the group which may be represented by the formula (Ba-1) and the group which may be represented by the formula (Ba-2) include the groups represented by the following formulae, and the like.

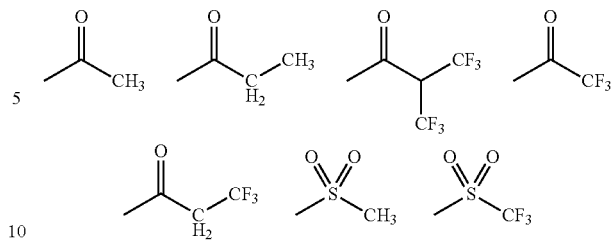

Examples of the structural unit (I) include structural units represented by the following formulae (1-1) to (1-18), and the like.

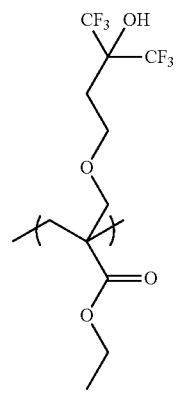

(1-1)

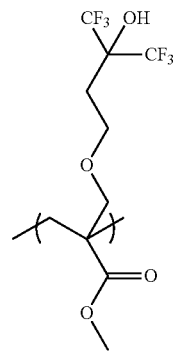

(1-2)

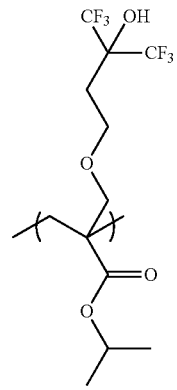

(1-3)

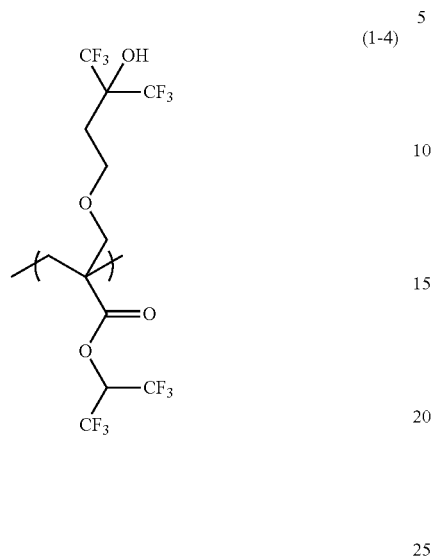
(1-4)
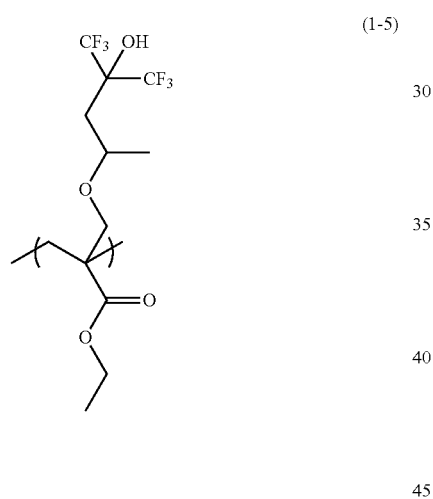
(1-5)
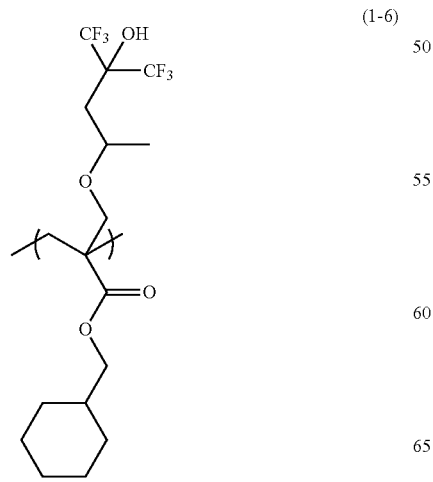
(1-6)
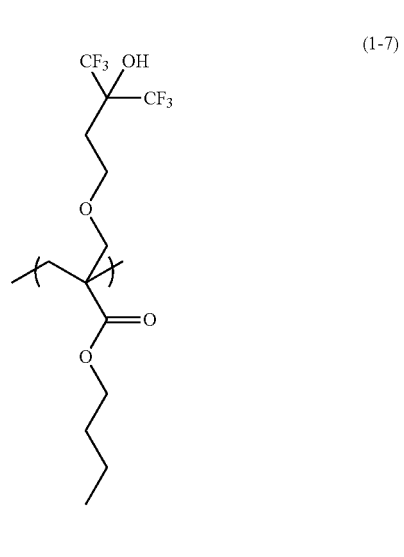
(1-7)
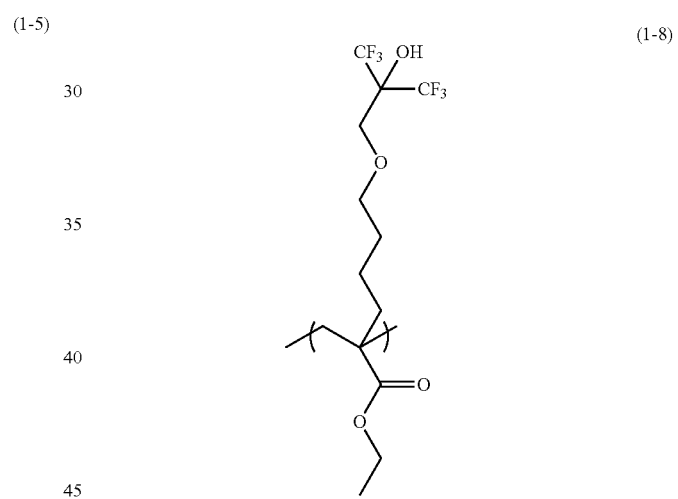
(1-8)
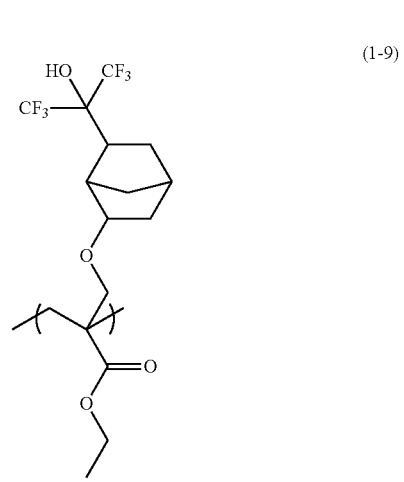
(1-9)

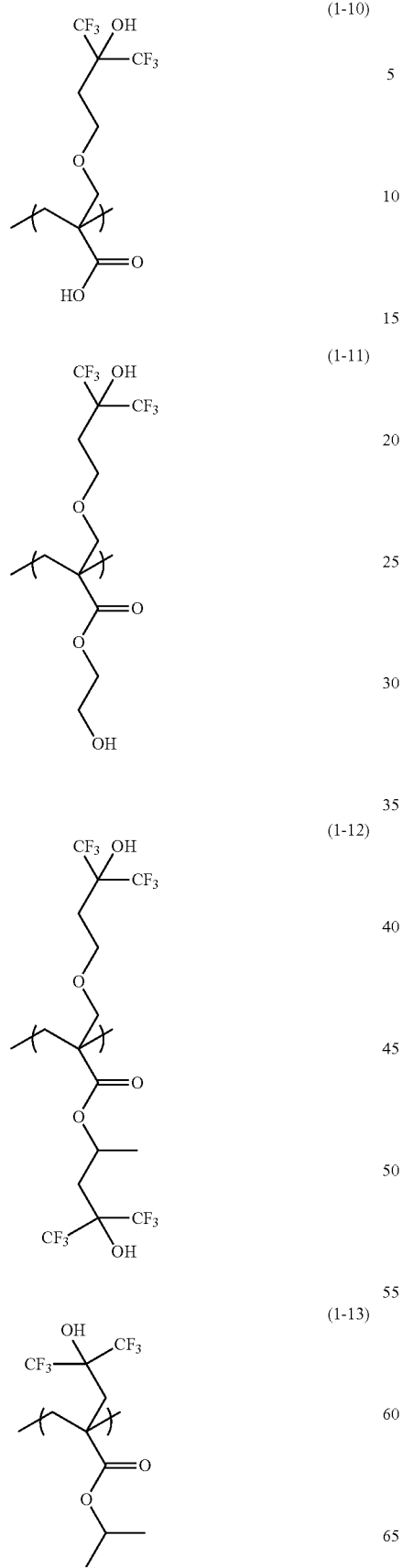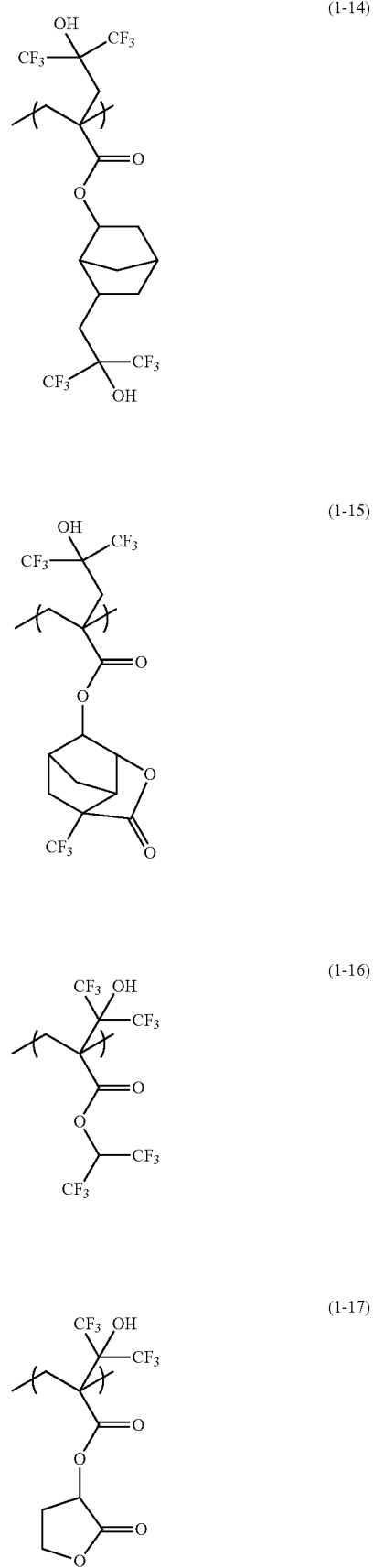

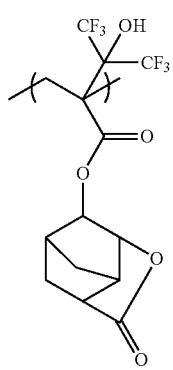

(1-18)

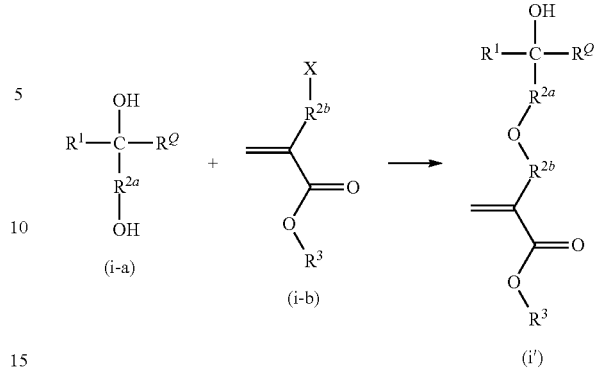

Among these, the structural units represented by the above formulae (1-1) to (1-9), (1-13) and (1-16) are preferred.

Moreover, examples of the structural unit (I) also include a structural unit derived from the structural units which may be represented by the above formulae (1-1) to (1-18) by substituting a hydrogen atom of a —$(CF_3)_2$C—OH group thereof with the monovalent base-labile group which may be represented by the formula (Ba-1) or (Ba-2); and the like.

The proportion of the structural unit (I) contained in the polymer component (A) with respect to the total structural units constituting the polymer component (A) falls within a range of preferably 1 mol % to 100 mol %, more preferably 4 mol % to 90 mol %, and still more preferably 10 mol % to 70 mol %. When the proportion of the structural unit (I) contained in the polymer component (A) falls within the above range, more superior water repellency of the resist upper layer film provided and more superior inhibitory effect on occurrence of defects such as bridge defects and blob defects in a resist pattern are exhibited.

Moreover, the proportion of the structural unit (I) contained in the polymer (a) with respect to the total structural units constituting the polymer (a) falls within a range of preferably 5 mol % to 100 mol %, more preferably 15 mol % to 100 mol %, and still more preferably 35 mol % to 85 mol %. When the proportion of the structural unit (I) contained in the polymer (a) falls within the above range, more superior water repellency of the resist upper layer film provided from the composition and more superior inhibitory effect on occurrence of defects such as bridge defects and blob defects in a resist pattern are exhibited.

The polymer component (A) can be obtained through radical polymerization of a monomer that gives the structural unit (I), and a monomer that gives other structural unit if necessary, as described later. In regard to a method for production of a compound that gives the structural unit (I), in the case of the following compound (i') that gives the structural unit (I) wherein $R^2$ represents —$R^{2a}$—O—$R^{2b}$— and $R^X$ represents a hydrogen atom, a method for production of the compound (i') is as described below, for example, and the compound (i') can be produced according to the following method. As the compound that gives the structural unit (I) wherein $R^2$ represents a group other than —$R^{2a}$—O—$R^{2b}$— and $R^X$ represents a hydrogen atom, well-known compounds may be used. Examples of the well-known compounds include compounds disclosed in Japanese Unexamined Patent Application, Publication Nos. 2002-220420, 2002-155112, and 2005-107476, and the like.

In the above formulae (i-a), (i-b) and (i'), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and X represents a halogen atom.

The reaction of the dihydroxy compound which may be represented by the above formula (i-a) with the haloalkylacrylic acid ester compound which may be represented by the above formula (i-b) in a solvent such as dichloromethane in the presence of a base compound such as triethylamine yields the compound (i') represented by the above formula. In the compound represented by the formula (i-a), of the two hydroxy groups, the reactivity of the hydroxy group bound to the carbon atom adjacent to the perfluoroalkyl group is lower, and therefore the compound (i) can be obtained in high yield.

Examples of the halogen atom which may be represented by X include a fluorine atom, a chlorine atom, a bromine atom, an iodine atom, and the like. Among these, a bromine atom is preferred in light of a reaction yield of the compound (i').

Among the monomers that give a structural unit (I), a compound that give a structural unit (I) wherein $R^X$ represents the monovalent base-labile group can be produced, for example, by the reaction for substituting the hydrogen atom of the hydroxy group of the compound (i') with $R^X$. For example, the reaction of a compound represented by the following formula with the compound (i'), for example, in the presence of a tertiary amine and the like can yield a compound (i) wherein $R^X$ represents a monovalent base-labile group which may be represented by the above formula (Ba-1). Moreover, the compound (i) wherein $R^X$ represents the monovalent base-labile group may be produced according to a reaction scheme for producing the compound (i') except that a compound that is provided by substituting a hydrogen atom of —$R^1R^QC$—OH of the compound (i-a) with $R^X$ is used in place of the compound (i-a) for the reaction with the compound (i-b).

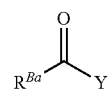

In the above formula, $R^{Ba}$ is as defined in the above formula (Ba-1); Y represents a halogen atom, a hydroxy group or RCOO; and R represents a monovalent organic group having 1 to 20 carbon atoms.

Structural Unit (II)

The structural unit (II) is a structural unit represented by the above formula (2). When the polymer component (A) further has a structural unit (II) that includes a fluorinated alkyl group, water repellency of the resist upper layer film provided from the composition for forming a resist upper layer film can be enhanced through the synergic effects between the structural unit (II) and the specific group (x) included in the structural unit (I).

In the above formula (2), $R^A$ represents a hydrogen atom, a methyl group, a fluorine atom or a trifluoromethyl group; and Rf represents a fluorinated hydrocarbon group having 1 to 20 carbon atoms.

Examples of the fluorinated hydrocarbon group having 1 to 20 carbon atoms which may be represented by Rf include a fluorinated linear hydrocarbon group having 1 to 20 carbon atoms, a fluorinated alicyclic hydrocarbon group having 3 to 20 carbon atoms, a fluorinated aromatic hydrocarbon group having 6 to 20 carbon atoms, and the like.

Examples of the fluorinated linear hydrocarbon group having 1 to 20 carbon atoms include:

a fluorinated alkyl group such as a trifluoromethyl group, a difluoroethyl group, a trifluoroethyl group, a perfluoroethyl group, a trifluoropropyl group, a hexafluoro-i-propyl group, a perfluoro-n-butyl group and a perfluoro-n-octyl group;

a fluorinated alkenyl group such as a trifluoroethenyl group and a trifluoropropenyl group;

a fluorinated alkynyl group such as a fluoroethynyl group and a trifluoropropynyl group; and the like.

Examples of the fluorinated alicyclic hydrocarbon group having 3 to 20 carbon atoms include:

a fluorinated cycloalkyl group such as a difluorocyclobutyl group, a tetrafluorocyclobutyl group, a tetrafluorocyclopentyl group, a nonafluorocyclopentyl group, a difluorocyclohexyl group and a difluoronorbornyl group;

a fluorinated cycloalkenyl group such as a difluorocyclobutenyl group and a difluoronorbornenyl group; and the like.

Examples of the fluorinated aromatic hydrocarbon group having 6 to 20 carbon atoms include:

a fluorinated aryl group such as a fluorophenyl group, a difluorophenyl group, a trifluorophenyl group, a pentafluorophenyl group, a fluorotolyl group, a fluoroxylyl group, a fluoronaphthyl group and a fluoroanthryl group;

a fluorinated aralkyl group such as a fluorobenzyl group, a difluorobenzyl group, a fluorophenethyl group and a fluoronaphthylmethyl group; and the like.

Among these, Rf preferably represents a fluorinated linear hydrocarbon group, more preferably a fluorinated alkyl group, and still more preferably a trifluoroethyl group and a hexafluoro-i-propyl group.

Examples of the structural unit (II) include structural units represented by the following formulae (2-1) to (2-6), and the like.

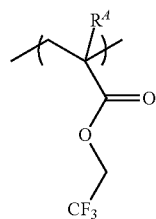

(2-1)

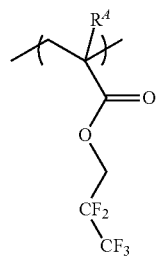

(2-2)

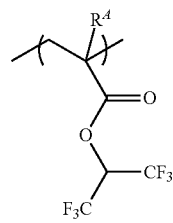

(2-3)

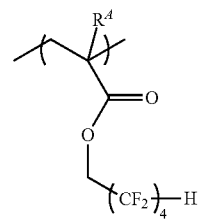

(2-4)

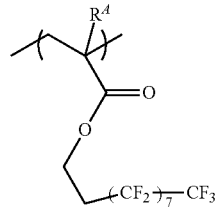

(2-5)

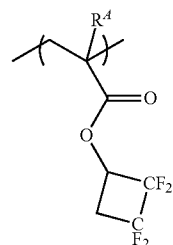

(2-6)

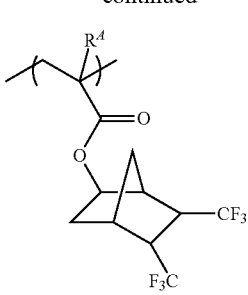

(2-7)

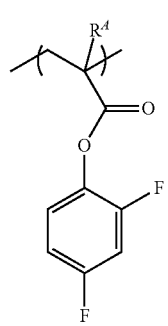

(2-8)

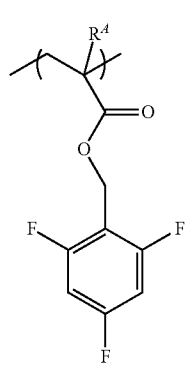

(2-9)

In the above formulae (2-1) to (2-6), $R^A$ is as defined in the above formula (2).

Among these, the structural unit represented by the formula (2-1) and the structural unit represented by the formula (2-3) are preferred.

The proportion of the structural unit (II) contained in the polymer component (A) with respect to the total structural units constituting the polymer component (A) falls within a range of preferably 0 mol % to 30 mol %, more preferably 1 mol % to 20 mol %, and still more preferably 2 mol % to 15 mol %. When the proportion of the structural unit (II) contained in the polymer component (A) falls within the above range, more superior water repellency and removability of the resist upper layer film provided from the composition for forming a resist upper layer film may be exhibited.

The proportion of the structural unit (II) contained in the polymer (a) with respect to the total structural units constituting the polymer (a) falls within a range of preferably 0 mol % to 70 mol %, more preferably 5 mol % to 65 mol %, and still more preferably 10 mol % to 60 mol %. When the proportion of the structural unit (II) contained in the polymer (a) falls within the above range, more superior water repellency and removability of the resist upper layer film provided from the composition for forming a resist upper layer film may be exhibited.

The proportion of the structural unit (II) contained in the polymer (b) with respect to the total structural units constituting the polymer (b) falls within a range of preferably 0 mol % to 70 mol %, more preferably 15 mol % to 65 mol %, and still more preferably 30 mol % to 60 mol %. When the proportion of the structural unit (II) contained in the polymer (b) falls within the above range, more superior water repellency and removability of the resist upper layer film provided from the composition for forming a resist upper layer film may be exhibited.

Structural Unit (III)

The structural unit (III) is a structural unit that includes a group represented by the above formula (3a) (except for the structural unit falling under the structural unit (I)) (hereinafter, may be also referred to as "structural unit (III-1)"), a structural unit that is other than the structural unit (I) and that includes a group represented by the above formula (3b) (hereinafter, may be also referred to as "structural unit (III-2)"), or a combination thereof. In the composition for forming a resist upper layer film, when the polymer component (A) has the structural unit (III), the water repellency and removability of the resist upper layer film provided from the composition can be improved.

In the above formula (3a), $R^N$ represents a fluorinated hydrocarbon group having 1 to 20 carbon atoms.

In the above formula (3b), $R^a$ represents a monovalent organic group having 1 to 20 carbon atoms; and $R^q$ represents a perfluoroalkyl group having 1 to 5 carbon atoms.

Examples of the fluorinated hydrocarbon group having 1 to 20 carbon atoms which may be represented by $R^N$ in the above formula (3a) include the same groups as those exemplified as the fluorinated hydrocarbon group having 1 to 20 carbon atoms which may be represented by Rf in the structural unit (II), and the like. Among these, a fluorinated alkyl group having 1 to 20 carbon atoms is preferred, a perfluoroalkyl group having 1 to 20 carbon atoms is more preferred, a perfluoroalkyl group having 1 to 4 carbon atoms is still more preferred, and a trifluoromethyl group is particularly preferred.

Examples of the structural unit (III-1) include a structural unit represented by the following formula (3-1) (hereinafter, may be also referred to as "structural unit (III-1a)"), and the like.

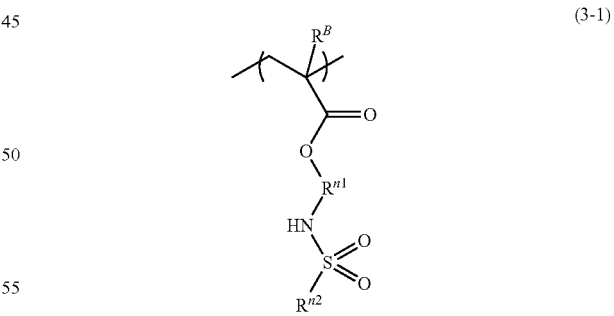

(3-1)

In the above formula (3-1), $R^B$ represents a hydrogen atom, a methyl group, a fluorine atom or a trifluoromethyl group; $R^{n1}$ represents a divalent linking group; and $R^{n2}$ represents a fluorinated alkyl group having 1 to 20 carbon atoms.

As $R^B$, a hydrogen atom and a methyl group are preferred and a methyl group is more preferred in light of copolymerizability of a monomer that gives the structural unit (III-1a), and the like.

Examples of the divalent linking group which may be represented by $R^{n1}$ include a divalent linear hydrocarbon group having 1 to 6 carbon atoms, a divalent alicyclic hydrocarbon group having 4 to 12 carbon atoms, and the like.

Examples of the divalent linear hydrocarbon group having 1 to 6 carbon atoms include a saturated linear hydrocarbon group such as a methanediyl group, a 1,2-ethanediyl group, a 1,1-ethanediyl group, a 1,3-propanediyl group, a 1,2-propanediyl group, a 1,1-propanediyl group, a 2,2-propanediyl group, a 1,4-butanediyl group, a 1,5-pentanediyl group, a 1,6-hexanediyl group, a 1-methyl-1,3-propanediyl group, a 2-methyl-1,3-propanediyl group, a 2-methyl-1,2-propanediyl group, a 1-methyl-1,4-butanediyl group and a 2-methyl-1,4-butanediyl group; an unsaturated linear hydrocarbon group such as a 1,2-ethenediyl group, a 1,3-propenediyl group and a 1,2-propenediyl group; and the like.

Examples of the divalent alicyclic hydrocarbon group having 4 to 12 carbon atoms include:

a monocyclic hydrocarbon group such as a cyclobutanediyl group such as a 1,3-cyclobutanediyl group; a cyclopentanediyl group such as a 1,3-cyclopentanediyl group; a cyclohexanediyl group such as a 1,4-cyclohexanediyl group and a 1,2-cyclohexanediyl group; and a cyclooctanediyl group such as a 1,5-cyclooctanediyl group;

a polycyclic hydrocarbon group such as a norbornanediyl group such as a 1,4-norbornanediyl group and a 2,5-norbornanediyl group, an adamantanediyl group such as a 1,3-adamantanediyl group and a 2,4-adamantanediyl group; and the like. Among these, a monocyclic hydrocarbon group is preferred, a cyclohexanediyl group is more preferred, and a 1,2-cyclohexanediyl group is still more preferred.

Among these, as $R^{r1}$, a divalent linear hydrocarbon group having 1 to 3 carbon atoms is preferred, and a 1,2-ethanediyl group is more preferred.

Examples of the fluorinated alkyl group having 1 to 20 carbon atoms which may be represented by $R^{r2}$ include a fluoromethyl group, a difluoromethyl group, a trifluoromethyl group, a trifluoroethyl group, a pentafluoroethyl group, a heptafluoropropyl group, a nonafluorobutyl group, and the like. Among these, a perfluoroalkyl group having 1 to 4 carbon atoms is preferred, and a trifluoromethyl group is more preferred.

Examples of the monovalent organic group having 1 to 20 carbon atoms which may be represented by $R^a$ in the above formula (3b) include the same groups as those exemplified as the monovalent organic group which may be represented by $R^1$ and $R^3$ in the structural unit (I), and the like. $R^a$ represents preferably a monovalent fluorinated hydrocarbon group having 1 to 20 carbon atoms, more preferably a fluorinated alkyl group having 1 to 20 carbon atoms, still more preferably a perfluoroalkyl group having 1 to 20 carbon atoms, particularly preferably a perfluoroalkyl group having 1 to 4 carbon atoms, and further particularly preferably a trifluoromethyl group.

Examples of the perfluoroalkyl group having 1 to 5 carbon atoms which may be represented by $R^q$ include the same group as the perfluoroalkyl group having 1 to 5 carbon atoms exemplified as $R^Q$ in the above formula (1), and the like. $R^q$ preferably represents a trifluoromethyl group.

The structural unit (III-2) is not particularly limited as long as the structural unit (III-2) is a structural unit that is other than the structural unit (I) and that includes the group (3b); the structural unit (III-2) is exemplified by a structural unit represented by the following formula (3-2) (hereinafter, may be also referred to as "structural unit (III-2a)"), and the like.

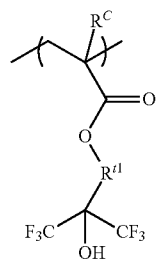

(3-2)

In the above formula (3-2), $R^C$ represents a hydrogen atom, a fluorine atom, a methyl group or a trifluoromethyl group; and $R^{r1}$ represents a divalent linking group.

$R^C$ represents preferably a hydrogen atom and a methyl group, and more preferably a methyl group in light of copolymerizability of a monomer that gives the structural unit (III-2a), and the like.

Examples of the divalent linking group which may be represented by $R^{r1}$ include the same groups as those exemplified as $R^{r1}$ in the above formula (3-1), and the like. Moreover, these linear hydrocarbon group and alicyclic hydrocarbon group may include an oxygen atom, a carbonyl group or an ester group between adjacent two carbon atoms of the same. $R^{r1}$ represents preferably a divalent linear hydrocarbon group having 1 to 3 carbon atoms and a divalent alicyclic hydrocarbon group having 4 to 12 carbon atoms, more preferably a propanediyl group, a divalent group having a cyclohexane skeleton, a divalent group having a norbornene skeleton and a divalent group having an adamantane skeleton, and still more preferably a 1,2-propanediyl group and a 1-cyclohexyl-1,2-ethanediyl group.

Examples of the structural unit (III-2a) include structural units represented by the following formulae (3-2-1) to (3-2-8), and the like.

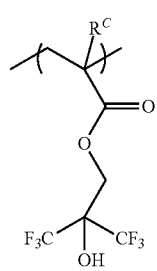

(3-2-1)

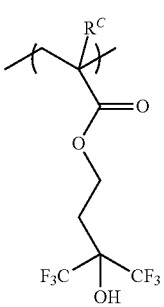

(3-2-2)

(3-2-3) 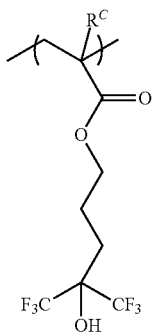

(3-2-4) 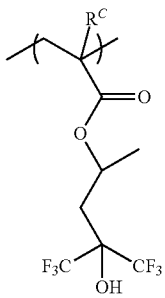

(3-2-5) 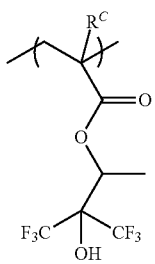

(3-2-6) 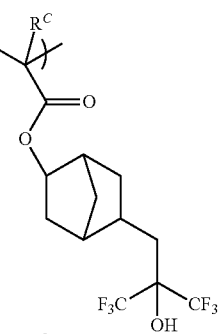

(3-2-7) 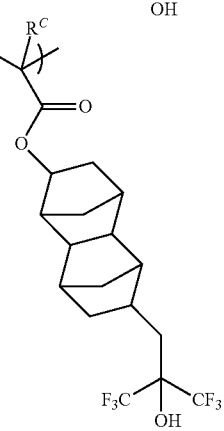

(3-2-8) 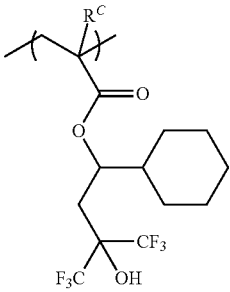

In the above formulae (3-2-1) to (3-2-8), $R^C$ is as defined in the above formula (3-2).

Among these, the structural unit represented by the formula (3-2-4) and the structural unit represented by the formula (3-2-8) are preferred.

The proportion of the structural unit (III) contained in the polymer component (A) with respect to the total structural units constituting the polymer component (A) falls within a range of preferably 0 mol % to 90 mol %, more preferably 1 mol % to 80 mol %, still more preferably 4 mol % to 75 mol %, and particularly preferably 20 mol % to 70 mol %. When the proportion of structural unit (III) contained in the polymer component (A) falls within the above range, the water repellency and upper layer film removability of the resist upper layer film provided from the composition for forming a resist upper layer film may be improved.

The proportion of the structural unit (III) contained in the polymer (a) with respect to the total structural units constituting the polymer (a) falls within a range of preferably 0 to 90 mol %, more preferably 5 mol % to 85 mol %, and still more preferably 15 mol % to 65 mol %. When the proportion of the structural unit (III) contained in the polymer (a) falls within the above range, the water repellency and upper layer film removability of the resist upper layer film provided from the composition for forming a resist upper layer film may be improved.

The proportion of the structural unit (III) contained in the polymer (b) with respect to the total structural units constituting the polymer (b) falls within a range of preferably 0 to 99 mol %, more preferably 5 mol % to 99 mol %, and still more preferably 30 mol % to 99 mol %. When the proportion of the structural unit (III) contained in the polymer (b) falls within the above range, the water repellency and upper layer film removability of the resist upper layer film provided from the composition for foaming a resist upper layer film may be improved.

Structural Unit (IV)

The structural unit (IV) is a structural unit that includes a sulfo group. Examples of the structural unit (IV) include a structural unit represented by the following formula (4), and the like.

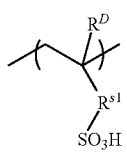 (4)

In the above formula (4), $R^D$ represents a hydrogen atom, a methyl group, a fluorine atom or a trifluoromethyl group; $R^{s1}$ represents a single bond, an oxygen atom, a sulfur atom, a divalent linear hydrocarbon group having 1 to 6 carbon atoms, a divalent alicyclic hydrocarbon group having 4 to 12 carbon atoms, a divalent aromatic hydrocarbon group having 6 to 12 carbon atoms or —C(=O)—X'—R'-group, wherein X' represents an oxygen atom, a sulfur atom or an NH group; and R' represents a divalent linear hydrocarbon group having 1 to 6 carbon atoms, a divalent alicyclic hydrocarbon group having 4 to 12 carbon atoms or a divalent aromatic hydrocarbon group having 6 to 12 carbon atoms.

$R^D$ preferably represents a hydrogen atom and a methyl group in light of copolymerizability of a monomer that gives the structural unit (IV), and the like.

Examples of the divalent linear hydrocarbon group having 1 to 6 carbon atoms and the divalent alicyclic hydrocarbon group having 4 to 12 carbon atoms which may be represented by $R^{s1}$ and R' include the same groups as those exemplified as $R^{n1}$ in the above formula (3-1), and the like.

Examples of the divalent aromatic hydrocarbon group having 6 to 12 carbon atoms which may be represented by $R^{s1}$ include an arylene group such as a phenylene group and a tolylene group, and the like.

$R^{s1}$ represents preferably a single bond, a divalent linear hydrocarbon group having 1 to 6 carbon atoms, a divalent aromatic hydrocarbon group having 6 to 12 carbon atoms, or —C(=O)—NH—R' wherein R' represents a divalent linear hydrocarbon group having 1 to 6 carbon atoms, more preferably a single bond, a methanediyl group, a phenylene group and —C(=O)—NH—CH(CH$_3$)—CH$_2$—, and still more preferably a single bond and —C(=O)—NH—CH(CH$_3$)—CH$_2$—.

Examples of the structural unit (IV) include structural units represented by the following formulae (4-1) to (4-4), and the like.

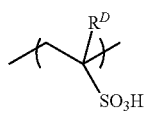

(4-1)

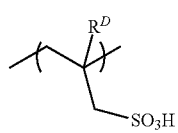

(4-2)

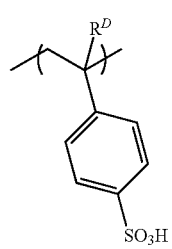

(4-3)

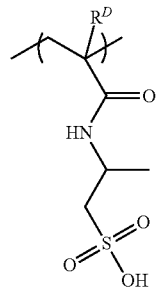

(4-4)

In the above formulae (4-1) to (4-4), $R^D$ is as defined in the above formula (4).

Among these, the structural unit represented by the above formula (4-1) and the structural unit represented by the above formula (4-4) are preferred.

The proportion of the structural unit (IV) contained in the polymer component (A) with respect to the total structural units constituting the polymer component (A) falls within a range of preferably 0 mol % to 10 mol %, more preferably 0.1 mol % to 5 mol %, and still more preferably 0.2 mol % to 2 mol %. When the proportion of the structural unit (IV) contained in the polymer component (A) falls within the above range, the occurrence of the blob defects may be further inhibited.

The proportion of the structural unit (IV) contained in the polymer (a) with respect to the total structural units constituting the polymer (a) falls within a range of typically 0 mol % to 20 mol %, more preferably 0.2 mol % to 10 mol %, and still more preferably 0.5 mol % to 7 mol %. When the proportion of the structural unit (IV) contained in the polymer (a) falls within the above range, the blob defects may be further inhibited.

The proportion of the structural unit (IV) contained in the polymer (b) with respect to the total structural units constituting the polymer (b) falls within a range of typically 0 mol % to 20 mol %, more preferably 0.2 mol % to 10 mol %, and still more preferably 0.5 mol % to 7 mol %. When the proportion of the structural unit (IV) contained in the polymer (b) falls within the above range, the blob defects may be further inhibited.

Structural Unit (V)

The structural unit (V) is a structural unit that includes a carboxy group (hereinafter, may be also referred to as "structural unit (V-1)"), a structural unit that includes a group represented by the above formula (v) (hereinafter, may be also referred to as "structural unit (V-2)"), or a combination thereof. When the polymer component (A) has the structural unit (V), removability and peel resistance of the resist upper layer film provided from the composition for forming a resist upper layer film can be improved.

Examples of the structural unit (V-1) include structural units represented by the following formulae (5-1-1) to (5-1-3) (hereinafter, may be also referred to collectively as "structural unit (V-1a)"), and the like.

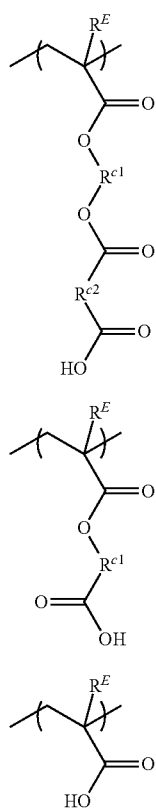 (5-1-1)

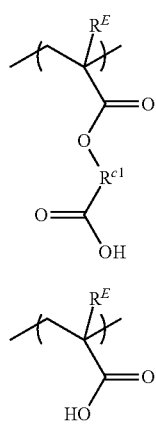 (5-1-2)

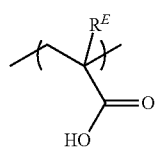 (5-1-3)

In the above formulae (5-1-1) to (5-1-3), $R^E$ represents a hydrogen atom, a fluorine atom, a methyl group or a trifluoromethyl group.

In the above formulae (5-1-1) and (5-1-2), $R^{c1}$ and $R^{c2}$ each independently represent a divalent linear hydrocarbon group having 1 to 6 carbon atoms, a divalent alicyclic hydrocarbon group having 4 to 12 carbon atoms or a divalent aromatic hydrocarbon group having 6 to 12 carbon atoms.

$R^E$ represents preferably a hydrogen atom and a methyl group, and more preferably a methyl group in light of copolymerizability of a monomer that gives the structural unit (V-1a), and the like.

Examples of the divalent linear hydrocarbon group having 1 to 6 carbon atoms which may be represented by $R^{c1}$ and $R^{c2}$ include the same groups as those exemplified as $R^{n1}$ in the above formula (3-1), and the like. Among these, a saturated linear hydrocarbon group is preferred, and a 1,2-ethanediyl group is more preferred.

Examples of the divalent alicyclic hydrocarbon group having 4 to 12 carbon atoms which may be represented by $R^{c1}$ and $R^{c2}$ include the same groups as those exemplified as $R^{n1}$ in the above formula (3-1), and the like. Among these, a monocyclic hydrocarbon group is preferred, a cyclohexanediyl group is more preferred, and a 1,2-cyclohexanediyl group is still more preferred.

Examples of the divalent aromatic hydrocarbon group having 6 to 12 carbon atoms which may be represented by $R^{c1}$ and $R^{c2}$ include the same groups as those exemplified as $R^{s1}$ in the above formula (4), and the like.

Examples of the structural unit (V-1a) include structural units represented by the following formulae (5-1-1-1) to (5-1-1-3), structural units represented by the following formulae (5-1-2-1) and (5-1-2-2), and the like.

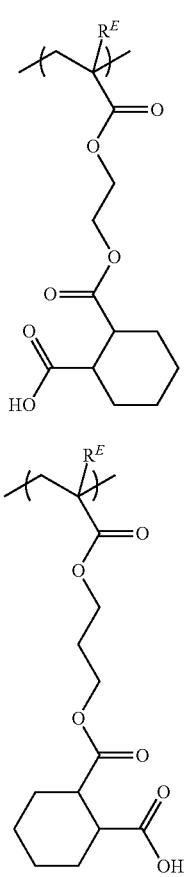 (5-1-1-1)

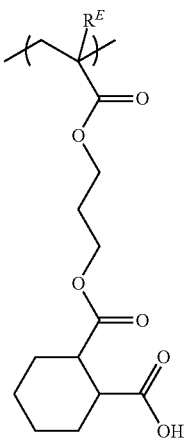 (5-1-1-2)

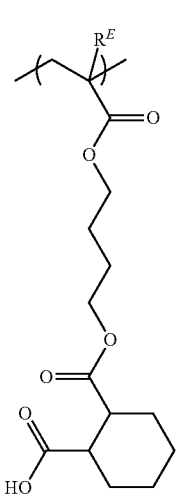 (5-1-1-3)

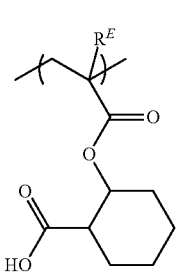 (5-1-2-1)

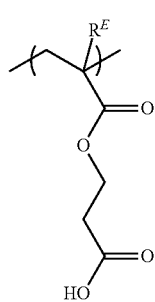

(5-1-2-2)

In the above formulae (5-1-1-1) to (5-1-2-2), $R^E$ is as defined in the above formulae (5-1-1) to (5-1-3).

The structural unit (V-1a) is preferably a structural unit represented by the formula (5-1-1) or a structural unit represented by the formula (5-1-3). Moreover, among structural units represented by the above formula (5-1-1), a structural unit represented by the formula (5-1-1-1) is more preferred.

The structural unit (V-2) is a structural unit that includes a group represented by the above formula (v) (hereinafter, may be also referred to as "group (v)").

In the above formula (v), $R^4$ represents a hydrogen atom, a halogen atom, a nitro group, an alkyl group, a monovalent alicyclic hydrocarbon group, an alkoxy group, an acyl group, an aralkyl group or an aryl group, wherein a part or all of hydrogen atoms included in the alkyl group, the alicyclic hydrocarbon group, the alkoxy group, the acyl group, the aralkyl group and the aryl group which are represented by $R^4$ are unsubstituted or substituted; $R^5$ represents —C(=O)—$R^6$, —S(=O)$_2$—$R^7$, —$R^8$—CN or —$R^9$—NO$_2$; $R^6$ and $R^7$ each independently represent a hydrogen atom, an alkyl group, a fluorinated alkyl group, a monovalent alicyclic hydrocarbon group, an alkoxy group, a cyano group, a cyanomethyl group, an aralkyl group or an aryl group, or $R^4$ and one of $R^6$ and $R^7$ taken together represent a ring structure, and the rest of $R^6$ and $R^7$ represents a hydrogen atom, an alkyl group, a fluorinated alkyl group, a monovalent alicyclic hydrocarbon group, an alkoxy group, a cyano group, a cyanomethyl group, an aralkyl group or an aryl group; and $R^8$ and $R^9$ each independently represent a single bond, a methylene group or an alkylene group having 2 to 5 carbon atoms.

Examples of the halogen atom which may be represented by $R^4$ include a fluorine atom, a chlorine atom, a bromine atom, an iodine atom, and the like. Among these, a fluorine atom and a chlorine atom are preferred.

Examples of the alkyl group which may be represented by $R^4$ include a linear alkyl group such as a methyl group, an ethyl group, a n-propyl group and a n-butyl group; a branched alkyl group such as an i-propyl group, an i-butyl group, a sec-butyl group and a t-butyl group; and the like. The alkyl group is preferably an alkyl group having 1 to 20 carbon atoms.

Examples of the monovalent alicyclic hydrocarbon group which may be represented by $R^4$ include a monocyclic alicyclic hydrocarbon group such as a cyclopentyl group and a cyclohexyl group; a polycyclic alicyclic hydrocarbon group such as an adamantyl group, a norbornyl group and a tetracyclodecanyl group; and the like. The alicyclic hydrocarbon group is preferably an alicyclic hydrocarbon group having 3 to 20 carbon atoms.

Examples of the alkoxy group which may be represented by $R^4$ include a methoxy group, an ethoxy group, and the like. The alkoxy group is preferably an alkoxy group having 1 to 20 carbon atoms.

Examples of the acyl group which may be represented by $R^4$ include an acetyl group, a propionyl group, and the like. The acyl group is preferably an acyl group having 2 to 20 carbon atoms.

Examples of the aralkyl group which may be represented by $R^4$ include a benzyl group, a phenethyl group, a naphthylmethyl group, and the like. The aralkyl group is preferably an aralkyl group having 7 to 12 carbon atoms.

Examples of the aryl group which may be represented by $R^4$ include a phenyl group, a tolyl group, a dimethylphenyl group, a 2,4,6-trimethylphenyl group, a naphthyl group, and the like. The aryl group is preferably an aryl group having 6 to 10 carbon atoms.

Examples of a substituent that may be included in the alkyl group, the monovalent alicyclic hydrocarbon group, the alkoxy group, the acyl group, the aralkyl group and the aryl group which may be represented by $R^4$ include a halogen atom such as a fluorine atom and a chlorine atom, a hydroxyl group, a nitro group, a cyano group, and the like.

Among these, as $R^4$, a hydrogen atom, an alkyl group having 1 to 5 carbon atoms, an alkoxy group having 1 to 5 carbon atoms and an acyl group having 2 to 5 carbon atoms are preferred, and a hydrogen atom, a methyl group, an ethyl group and an acetyl group are more preferred in light of a balance of the solubility in a developer solution and the peel resistance of the resist upper layer film provided from the composition for forming a resist upper layer film.

In a case where $R^5$ represents —C(=O)—$R^6$ and —S(=O)$_2$—$R^7$, examples of an alkyl group, a monovalent alicyclic hydrocarbon group, an alkoxy group, an aralkyl group and an aryl group which may be represented by $R^6$ and $R^7$ include the same groups as the alkyl group, the monovalent alicyclic hydrocarbon group, the alkoxy group, the aralkyl group and the aryl group exemplified as the respective groups which may be represented by $R^4$, and the like. Moreover, examples of the fluorinated alkyl group which may be represented by $R^6$ and $R^7$ include a group derived from the group exemplified as the alkyl group which may be represented by $R^4$ by substituting at least one of hydrogen atoms included therein with a fluorine atom, and the like. Among these, $R^6$ and $R^7$ represent preferably a hydrogen atom and an alkyl group, and more preferably a hydrogen atom, a methyl group and an ethyl group.

The ring structure-containing group represented by $R^4$ and one of $R^6$ and $R^7$ taken together is preferably a divalent alicyclic hydrocarbon group having 5 to 12 carbon atoms which includes the carbon atom to which each of $R^4$ and one of $R^6$ and $R^7$ bond, as well as an oxo group.

In a case where $R^5$ represents —$R^8$—CN and —$R^9$—NO$_2$, $R^8$ and $R^9$ preferably represents a single bond, a methanediyl group or an ethanediyl group.

Groups represented by the following formulae (v-1) to (v-8) are preferred as the group (v).

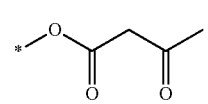

(v-1)

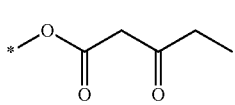

(v-2)

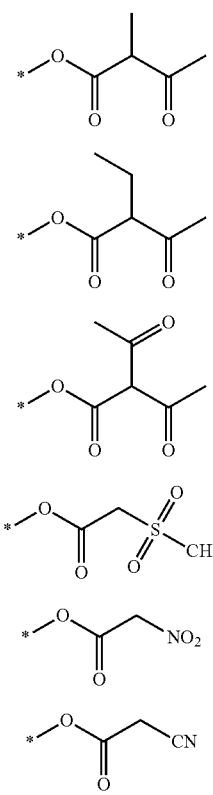

(v-3)
(v-4)
(v-5)
(v-6)
(v-7)
(v-8)

In the above formulae (v-1) to (v-8), * denotes a binding site.

Examples of the structural unit (V-2) include a structural unit derived from, for example, a (meth)acrylic acid ester derivative that includes the group (v), a (meth)acrylamide derivative that includes the group (v), a vinyl ether derivative that includes the group (v), an olefin derivative that includes the group (v), a styrene derivative that includes the group (v), and the like. Among these, a structural unit derived from a (meth)acrylic acid ester derivative is preferred. In other words, a structural unit (V-2a) represented by the following formula (5-2) is preferred as the structural unit (V-2).

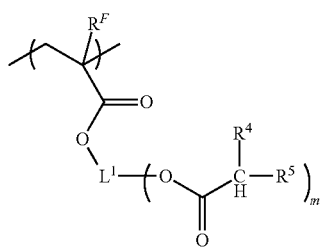

(5-2)

In the above formula (5-2), $R^4$ and $R^5$ are as defined in the above formula (v); m is an integer of 1 to 3, wherein in a case where $R^4$ and $R^5$ are each present in a plurality of number, a plurality of $R^4$s are the same or different with each other and a plurality of $R^5$s are the same or different with each other; $L^1$ represents a linking group having a valency of (m+1); and $R^F$ represents a hydrogen atom, a methyl group, a fluorine atom or a trifluoromethyl group.

$R^F$ represents preferably a hydrogen atom and a methyl group, and more preferably a methyl group in light of copolymerizability of a monomer that gives the structural unit (V-2a), and the like.

In regard to the linking group having a valency of (m+1) which may be represented by $L^1$, examples of a divalent linking group (in the case where m is 1) include an alkanediyl group, a divalent alicyclic hydrocarbon group, an alkenediyl group, an arenediyl group, and the like. It is to be noted that a part or all of hydrogen atoms included in these groups are unsubstituted or substituted with a halogen atom such as a fluorine atom and a chlorine atom, and a cyano group, and the like.

Examples of the alkanediyl group include a methanediyl group, an ethanediyl group, a propanediyl group, a butanediyl group, a hexanediyl group, an octanediyl group, and the like. The alkanediyl group is preferably an alkanediyl group having 1 to 8 carbon atoms.

Examples of the divalent alicyclic hydrocarbon group include a monocyclic alicyclic hydrocarbon group such as a cyclopentanediyl group and a cyclohexanediyl group; a polycyclic alicyclic hydrocarbon such as a norbornanediyl group and an adamantanediyl group; and the like. The divalent alicyclic hydrocarbon group is preferably an alicyclic hydrocarbon group having 5 to 12 carbon atoms.

Examples of the alkenediyl group include an ethenediyl group, a propenediyl group, a butenediyl group, and the like. The alkenediyl group is preferably an alkenediyl group having 2 to 6 carbon atoms.

Examples of the arenediyl group include a phenylene group, a tolylene group, a naphthylene group, and the like. The arenediyl group is preferably an arenediyl group having 6 to 15 carbon atoms.

Among these, $L^1$ represents preferably an alkanediyl group, a divalent alicyclic hydrocarbon group, and more preferably an alkanediyl group having 1 to 4 carbon atoms and a divalent alicyclic hydrocarbon group having 6 to 11 carbon atoms. $L^1$ preferably represents a divalent alicyclic hydrocarbon group in light of the enhancement of the water repellency of the resultant resist upper layer film.

Structural units represented by the following formulae (5-2-1) to (5-2-10) are preferred as the structural unit (V-2a).

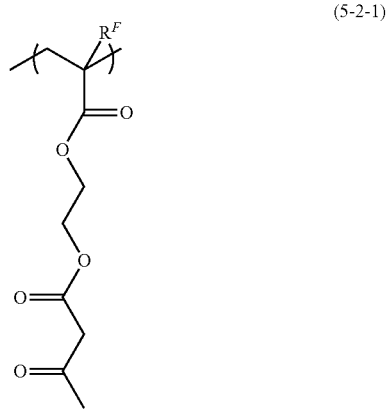

(5-2-1)

(5-2-2)
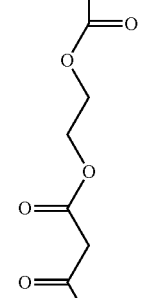
(5-2-3)
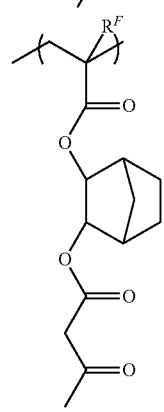
(5-2-4)
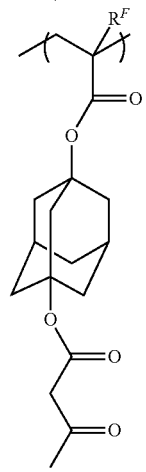
(5-2-5)
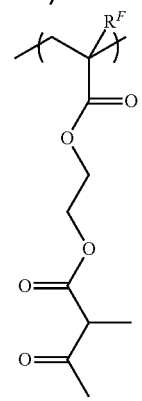
(5-2-6)
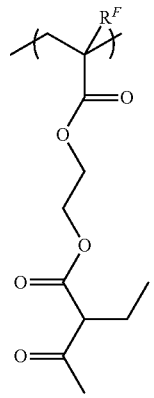
(5-2-7)
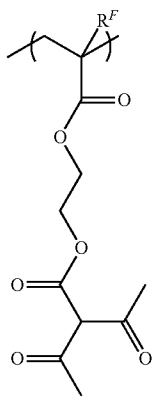
(5-2-8)
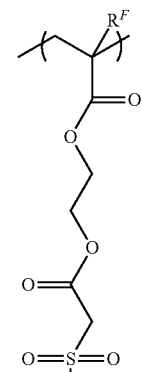
(5-2-9)
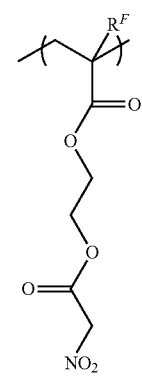

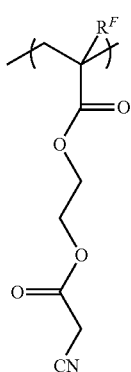

(5-2-10)

In the above formulae (5-2-1) to (5-2-10), $R^F$ is as defined in the above formula (5-2).

The proportion of the structural unit (V) contained in the polymer component (A) with respect to the total structural units constituting the polymer component (A) falls within a range of preferably 0 mol % to 30 mol %, more preferably 1 mol % to 20 mol %, and still more preferably 4 mol % to 15 mol %. When the proportion of the structural unit (V) contained in the polymer component (A) falls within the above range, the removability and peel resistance of the resist upper layer film provided from the composition for forming a resist upper layer film may be improved.

The proportion of the structural unit (V) contained in the polymer (a) with respect to the total structural units constituting the polymer (a) falls within a range of preferably 0 mol % to 60 mol %, more preferably 10 mol % to 55 mol %, and still more preferably 25 mol % to 50 mol %. When the proportion of the structural unit (V) contained in the polymer (a) falls within the above range, the removability and peel resistance of the resist upper layer film provided from the composition for forming a resist upper layer film may be improved.

The proportion of the structural unit (V) contained in the polymer (b) with respect to the total structural units constituting the polymer (b) falls within a range of preferably 0 mol % to 60 mol %, more preferably 3 mol % to 40 mol %, and still more preferably 5 mol % to 30 mol %. When the proportion of the structural unit (V) contained in the polymer (b) falls within the above range, the removability and peel resistance of the resist upper layer film provided from the composition for forming a resist upper layer film may be improved.

Other Structural Unit

The polymer component (A) may include other structural unit, in addition to the structural units (I) to (V), in a polymer which is identical to or different from the polymer (a). Examples of the other structural unit include a structural unit that includes a phenolic hydroxyl group, and the like. Examples of the structural unit that includes a phenolic hydroxyl group include a structural unit that includes a phenol structure, a structural unit that includes a naphthol structure, and the like, and more specifically a structural unit derived from hydroxystyrene, a structural unit derived from a vinylhydroxynaphthalene, a structural unit derived from (meth)acrylic acid hydroxyphenyl ester, a structural unit derived from (meth)acrylic acid hydroxynaphthyl ester, and the like. Moreover, the other structural unit is exemplified by a structural unit derived from an alkyl(meth)acrylate such as propyl(meth)acrylate, butyl(meth)acrylate and lauryl(meth)acrylate in light of improvement of the water repellency of the resist upper layer film; and a structural unit that includes an acid-labile group in light of controlling, for example, the molecular weight, the glass transition point and the solubility in a solvent of the polymer component (A); and the like. The proportion of the other structural unit contained in the polymer component (A) with respect to the total structural units constituting the polymer component (A) is typically no greater than 30 mol %, and preferably no greater than 20 mol %. The proportion of the other structural unit contained in the polymer (a) with respect to the total structural units constituting the polymer (a) is typically no greater than 30 mol %, and preferably no greater than 20 mol %. The proportion of the other structural unit contained in the polymer (b) with respect to the total structural units constituting the polymer (b) is typically no greater than 30 mol %, and preferably no greater than 20 mol %.

The mass ratio of the polymer (a) to the polymer (b) in the polymer component (A) (the polymer (a)/the polymer (b)) is preferably 5/95 to 100/0, more preferably 7/93 to 90/10, still more preferably 10/90 to 80/20, and particularly preferably 20/80 to 70/30.

Method for Synthesis of Polymer Component (A)

The polymer (a) and the polymer (b) constituting the polymer component (A) can be synthesized, for example, by subjecting a predetermined monomer to polymerization such as radical polymerization in a polymerization solvent in the presence of an appropriately selected polymerization initiator and/or chain transfer agent.

Examples of the polymerization solvent include:

alcohols such as methanol, ethanol, 1-propanol, 2-propanol, 1-butanol, 2-butanol, ethylene glycol, diethylene glycol and propylene glycol;

cyclic ethers such as tetrahydrofuran and dioxane;

alkyl ethers of polyhydric alcohols such as ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, diethylene glycol ethyl methyl ether, propylene glycol monomethyl ether and propylene glycol monoethyl ether;

alkyl ether acetates of polyhydric alcohols such as ethylene glycol ethyl ether acetate, diethylene glycol ethyl ether acetate, propylene glycol ethyl ether acetate and propylene glycol monomethyl ether acetate;

aromatic hydrocarbons such as toluene and xylene;

ketones such as acetone, methyl ethyl ketone, methyl isobutyl ketone, cyclohexanone, 4-hydroxy-4-methyl-2-pentanone and diacetone alcohol;

esters such as ethyl acetate, butyl acetate, methyl 2-hydroxypropionate, ethyl 2-hydroxy-2-methylpropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate and methyl 3-ethoxypropionate; and the like. Among these, cyclic ethers, alkyl ethers of polyhydric alcohols, alkyl ether acetates of polyhydric alcohols, ketones or esters are preferred. It is to be noted that the polymerization solvent may be used either alone, or in combination of two or more types thereof.

The polystyrene equivalent weight average molecular weight (Mw) of the polymer component (A) as determined by gel permeation chromatography (GPC) is preferably 2,000 to 50,000, more preferably 3,000 to 30,000, still more preferably 5,000 to 20,000, and particularly preferably 8,000 to 13,000. When the Mw of the polymer component (A) is no less than 2,000, water resistance and mechanical characteristics as a resist upper layer film can be favorably improved, whereas when the Mw is no greater than 50,000, solubility of the polymer in a solvent can be increased. The Mw of the polymer (a) is preferably 2,000 to 50,000, more preferably 3,000 to 30,000, and still more preferably 5,000 to 20,000. When the Mw of the polymer (a) is no less than 2,000, water resistance and mechanical characteristics as a resist upper layer film can be favorably improved, whereas when the Mw is no greater than 50,000, solubility of the polymer in a solvent can be increased.

The ratio (Mw/Mn) of the Mw to the polystyrene equivalent number average molecular weight (Mn) as determined by GPC of the polymer component (A) is preferably 1 to 5, more preferably 1 to 3, and still more preferably 1 to 2.5. The Mw/Mn of the polymer (a) is preferably 1 to 5, more preferably 1 to 3, and still more preferably 1 to 2.5.

Preferably, the composition for forming a resist upper layer film contains impurities such as halogen ions and metals in an amount as low as possible. A decrease in the amount of the impurities can lead to improvement of coating properties as a composition for forming a resist upper layer film, and of uniform dissolution of a resist upper layer film in an alkaline developer solution. Examples of a method for purifying the polymer component (A) to lessen the impurities includes, a chemical purification technique such as, for example, water-rinsing, liquid-liquid extraction, and filtration through a demetallizing filter, a combination of the chemical purification technique and a physical purification technique such as ultrafiltration and centrifugal separation, and the like.

The content of the polymer component (A) with respect to the total solid content of the composition for forming a resist upper layer film is preferably 70% by mass to 100% by mass, more preferably 80% by mass to 100% by mass, and still more preferably 90% by mass to 100% by mass.

(B) Solvent

The composition for forming a resist upper layer film according to the embodiment of the present invention contains a solvent (B). Any solvent may be used as the solvent (B) as long as it can dissolve or disperse the polymer component (A) and the optional component contained as required; a solvent hardly causing impairment of lithography performances due to excessive intermixing with a resist film and the like, during the coating of the composition for forming a resist upper layer film on the resist film can be suitably used.

Examples of the solvent (B) include an alcohol solvent, an ether solvent, a hydrocarbon solvent, a ketone solvent, an ester solvent, water, and the like.

Examples of the alcohol solvent include:
monohydric alcohols such as butanol and pentanol;
polyhydric alcohols such as ethylene glycol and propylene glycol; and the like.

Examples of the ether solvent include:
partial alkyl ethers of polyhydric alcohols such as ethylene glycol monomethyl ether and ethylene glycol monoethyl ether;
alkyl ethers of polyhydric alcohols such as ethylene glycol dimethyl ether, ethylene glycol methyl ethyl ether, ethylene glycol diethyl ether and diethylene glycol dimethyl ether;
alkyl ether acetates of polyhydric alcohols such as ethylene glycol monomethyl ether acetate, ethylene glycol monoethyl ether acetate, diethylene glycol monomethyl ether acetate and diethylene glycol monoethyl ether acetate;
aliphatic ethers such as diethyl ether, dipropyl ether, dibutyl ether, butyl methyl ether, butyl ethyl ether, diisoamyl ether, hexyl methyl ether, octyl methyl ether, cyclopentyl methyl ether and dicyclopentyl ether;
aliphatic-aromatic ethers such as anisole and phenyl ethyl ether;
cyclic ethers such as tetrahydrofuran, tetrahydropyran and dioxane; and the like.

Examples of the hydrocarbon solvent include:
lower hydrocarbons such as hexane, cyclohexane and heptane;
higher hydrocarbons such as decane, dodecene and undecane; and the like.

Examples of the ketone solvent include:
dialkylketones such as acetone and methyl ethyl ketone;
cyclic ketones such as cyclopentanone and cyclohexanone; and the like.

Examples of the ester solvent include ethyl acetate, butyl acetate, and the like.

Among these, an alcohol solvent and an ether solvent are preferred; a monohydric alcohol, an aliphatic ether, a cyclic ether, a partial alkyl ether of a polyhydric alcohol, an alkyl ether of a polyhydric alcohol and an alkyl ether acetate of a polyhydric alcohol are more preferred; a monohydric alcohol having 4 to 10 carbon atoms, an aliphatic ether having an alkyl chains having 4 to 10 carbon atoms are still more preferred; and 4-methyl-2-pentanol and diisoamyl ether are particularly preferred. The ether solvent is preferred since when the ether solvent is contained in the solvent (B), it leads to lowering of the viscosity of the composition for forming a resist upper layer film, an effective reduction of the amount of the composition coated, and consequently a cost reduction.

Optional Component

The composition for forming a resist upper layer film may contain an optional component in addition to the polymer (A) and the solvent (B). Examples of the other optional component include a surfactant, and the like.

Examples of the surfactant include commercially available fluorochemical surfactants such as BM-1000, BM-1100 (each manufactured by BM Chemie) and Megaface F142D, F172, F173, F183 (each manufactured by Dainippon Ink And Chemicals, Incorporated), and the like. The amount of the surfactant contained with respect to 100 parts by mass of the polymer component (A) is preferably no greater than 5 parts by mass.

Method for Preparation of Composition for Forming Resist Upper Layer Film

The composition for forming a resist upper layer film may be prepared, for example, by mixing the polymer component (A), and the optional component as required, with solvent (B) to dissolve the same. The solid content concentration of the composition for forming a resist upper layer film is typically 0.5% by mass to 30% by mass, and preferably 1% by mass to 20% by mass.

The composition for forming a resist upper layer film enables a resist upper layer film exhibiting superior water repellency to be provided and occurrence of defects such as bridge defects and blob defects in a resist pattern to be inhibited, as mentioned above, and therefore the composition for farming a resist upper layer film can be suitably used for the provision of a resist upper layer film that is provided on a resist film through lamination. In addition, in a case where the composition for forming a resist upper layer film is used for an exposure through a liquid immersion medium, elution of a resist film component into a liquid immersion liquid can be inhibited to a greater extent due to superior water repellency of the resist upper layer film, and moreover, high speed scanning may be permitted due to an exhibited large receding contact angle. Moreover, in a case where the composition for forming a resist upper layer film is used for an exposure to an EUV or an exposure to an electron beam, outgassing from the resist film can be inhibited to a greater extent due to superior water repellency of the resist upper layer film, and moreover, lithography performances such as local CDU of the resultant resist pattern can be improved. Thus, the composition for forming a resist upper layer film can be suitably used for, in particular, an exposure through a liquid immersion medium, an exposure to an EUV or an exposure to an electron beam.

Compound

A compound according to an embodiment of the present invention is represented by the above formula (i). As a result of having the specific structure, the compound can be suitably used as, for example, a monomer that gives a polymer constituting the composition for forming a resist upper layer film.

In the above formula (i), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

In the compound, examples of the divalent linear hydrocarbon group having 1 to 16 carbon atoms which may be represented by $R^{2a}$ include a methanediyl group, an ethanediyl group, a propanediyl group, a butanediyl group, a pentanediyl group, a hexanediyl group, an octanediyl group, a decanediyl group, a dodecanediyl group, a tetradecanediyl group, a hexadecanediyl group, and the like.

Examples of the group obtained by combining —O— with the divalent linear hydrocarbon group having 1 to 16 carbon atoms groups which may be represented by $R^{2a}$ include an alkanediyloxy group having 1 to 16 carbon atoms such as a methanediyloxy group, an ethanediyloxy group, a propanediyloxy group, a butanediyloxy group, a pentanediyloxy group, a hexanediyloxy group, an octanediyloxy group; a group having 1 to 16 carbon atoms and one —O— unit such as a methanediyloxymethanediyl group, a methanediyloxyethanediyl group, a methanediyloxy(1,2-propanediyl) group and a methanediyloxybutanediyl group; a group having 1 to 16 carbon atoms and two or more —O— units such as a propanediyloxyethanediyloxyethanediyl group, and the like.

Examples of the compound according to the embodiment of the present invention include compounds represented by the following formulae (i-1) to (i-12), and the like. Moreover, the compound according to the embodiment of the present invention is exemplified by compounds derived from the compounds represented by the following formulae (i-1) to (i-12) by substituting a hydrogen atom of a —(CF$_3$)$_2$C—OH group thereof with the monovalent base-labile group represented by the above formula (Ba-1) or (Ba-2); and the like.

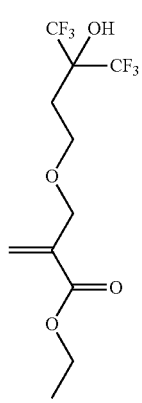

(i-1)

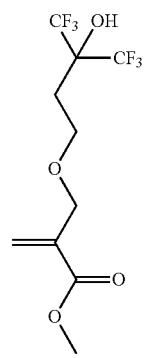

(i-2)

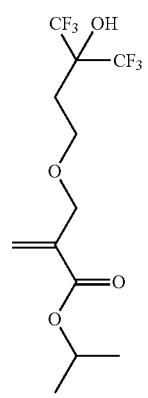

(i-3)

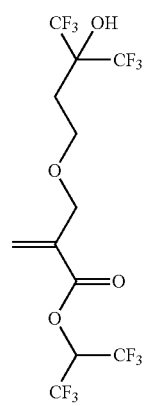

(i-4)

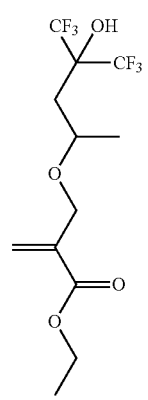

(i-5)

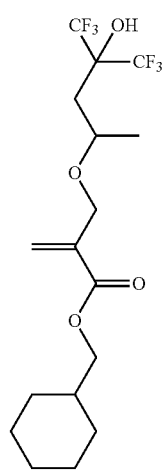
(i-6)
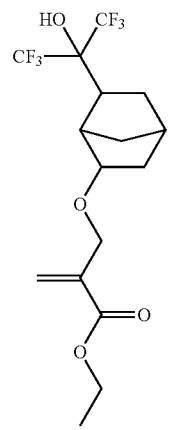
(i-9)
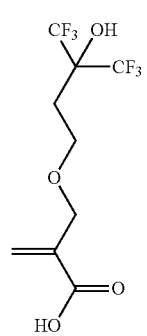
(i-7)
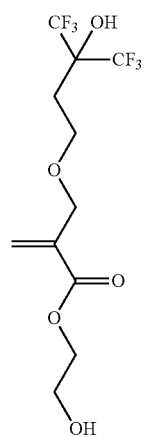
(i-10)
(i-8)
(i-11)

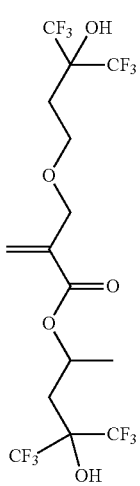

(i-12)

Among these, the compounds represented by the above formulae (i-1) to (i-7) are preferred as the compound according to the embodiment of the present invention.

Method for Production of Compound

A method for producing the compound represented by the above formula (i') according to the embodiment of the present invention includes:

reacting a dihydroxy compound represented by the formula (i-a) with a haloalkylacrylic acid ester compound represented by the formula (i-b). According to the method for production, the compound represented by the above formula (i') can be produced conveniently and in high yield.

In the above formulae (i-a), (i-b) and (i'), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and X represents a halogen atom.

Polymer

A polymer according to an embodiment of the present invention has a structural unit (I-A) represented by the above formula (1A). Since the polymer has the specific structural unit, the polymer can be suitably used as, for example, a polymer component constituting the composition for forming a resist upper layer film.

In the above formula (1A), $R^1$ represents a hydrogen atom or a monovalent organic group having 1 to 20 carbon atoms; $R^{2a}$ represents a divalent linear hydrocarbon group having 1 to 16 carbon atoms, or a group obtained by combining —O— with the divalent linear hydrocarbon group; $R^{2b}$ represents a divalent hydrocarbon group having 1 to 10 carbon atoms; $R^3$ represents a hydrogen atom or a monovalent organic group having 1 to 20 carbon atoms; $R^Q$ represents a perfluoroalkyl group having 1 to 5 carbon atoms; and $R^X$ represents a hydrogen atom or a monovalent base-labile group.

The compound, the method for production of the compound and the polymer according to the embodiments of the present invention have been described in the section of the polymer (a) of the polymer component (A) in the composition for forming a resist upper layer film, and the like, and therefore the explanation thereof is omitted here.

Resist Pattern-Forming Method

A resist pattern-forming method according to an embodiment of the present invention includes:

(1) providing a resist film using a photoresist composition;

(2) providing a resist upper layer film on the resist film using the composition for forming a resist upper layer film according to the embodiment of the present invention;

(3) exposing the resist film having the resist upper layer film provided thereon; and (4) developing the exposed resist film.

The exposure in the step (3) is preferably carried out through a liquid immersion medium.

Moreover, an exposure light in the step (3) is preferably a far ultraviolet ray, an EUV or an electron beam.

According to the resist pattern-forming method, a resist upper layer film exhibiting superior water repellency can be provided and occurrence of defects such as bridge defects and blob defects in a resist pattern can be inhibited as a result of the use of the composition for forming a resist upper layer film according to the embodiment of the present invention. Hereinafter, each step will be explained.

Step (1)

In the step (1), a resist film is provided by coating a photoresist composition on a substrate. A silicon wafer, a silicon wafer coated with aluminum, and the like are typically used as the substrate. Moreover, in order to maximally utilize the characteristics of the resist film, it is also preferred to preform, for example, an organic or inorganic antireflective film as disclosed in, for example, Japanese Examined Patent Application, Publication No. H6-12452 and the like on the surface of the substrate.

The type of the photoresist composition is not particularly limited, and the photoresist composition can be appropriately selected from among photoresist compositions conventionally used to provide a resist film, depending on intended uses of the resist. Among these, a photoresist composition containing (P) a polymer that includes an acid-labile group and (Q) an acid generating agent is preferred, and in particular a positive type photoresist composition is preferred.

In the polymer (P), examples of a structural unit that includes an acid-labile group (hereinafter, may be also referred to as "structural unit (p)") include structural units represented by the following formulae (p-1) and (p-2), and the like.

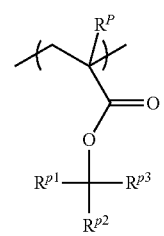

(p-1)

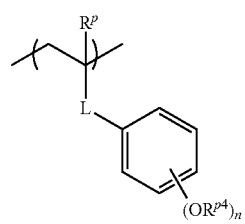

(p-2)

In the above formula (p-1), $R^P$ represents a hydrogen atom, a fluorine atom, a methyl group or a trifluoromethyl group; $R^{p1}$ represents a monovalent linear hydrocarbon group having 1 to 10 carbon atoms; and $R^{p2}$ and $R^{p3}$ represent a monovalent linear hydrocarbon group having 1 to 10 carbon atoms or a monovalent alicyclic hydrocarbon group having 3 to 20 carbon atoms, or taken together represent a ring structure having 3 to 20 carbon atoms together with the carbon atom to which $R^{p2}$ and $R^{p3}$ bond.

In the above formula (p-2), $R^P$ represents a hydrogen atom, a fluorine atom, a methyl group or a trifluoromethyl group; L represents a single bond, —COO— or —CONH—; $R^{p4}$ represents a group that is dissociated by an action of an acid and gives rise to a phenolic hydroxyl group; and n is an integer of 1 to 5, wherein in a case where n is no less than 2, a plurality of $R^{p4}$s are a same or different.

In the above formula (p-1), $R^P$ represents preferably a hydrogen atom and a methyl group, and more preferably a methyl group in light of copolymerizability of a monomer that gives the structural unit (p).

Examples of the monovalent linear hydrocarbon group having 1 to 10 carbon atoms which may be represented by $R^{p1}$, $R^{p1}$ and $R^{p3}$ include an alkyl group such as a methyl group, an ethyl group, a n-propyl group, an i-butyl group and a n-butyl group, and the like.

Examples of the monovalent alicyclic hydrocarbon group having 3 to 20 carbon atoms which may be represented by $R^{p2}$ and $R^{p3}$ include a monocyclic cycloalkyl group such as a cyclobutyl group, a cyclopentyl group and a cyclohexyl group; a polycyclic cycloalkyl group such as a norbornyl group and an adamantyl group; and the like.

Examples of the ring structure having 3 to 20 carbon atoms which may be taken together represented by $R^{p2}$ and $R^{p3}$ together with the carbon atom to which they bond include a monocyclic cycloalkane structure such as a cyclopentane structure and a cyclohexane structure; a polycyclic cycloalkane structure such as a norbornane structure and an adamantane structure, and the like.

In the above formula (p-2), $R^P$ represents preferably a hydrogen atom and a methyl group, and more preferably a hydrogen atom in light of copolymerizability of a monomer that gives the structural unit (p).

Examples of the group which may be represented by $R^{p4}$ and is dissociated by an action of an acid and gives rise to a phenolic hydroxyl group include a group represented by the following formula (p-2-1), a group represented by the following formula (p-2-2), and the like.

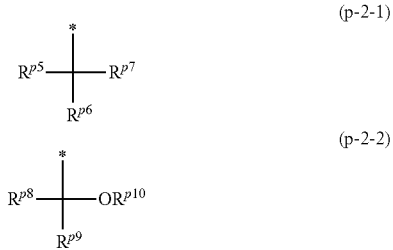

In the above formula (p-2-1), $R^{p5}$, $R^{p6}$ and $R^{p7}$ each independently represent an alkyl group having 1 to 5 carbon atoms.

In the above formula (p-2-2), $R^{p8}$, $R^{p9}$ and $R^{p10}$ each independently represent an alkyl group having 1 to 5 carbon atoms.

In the above formulae (p-2-1) and (p-2-2), * denotes a site of bonding to the oxygen atom.

Examples of the alkyl group having 1 to 5 carbon atoms which may be represented by $R^{p5}$, $R^{p6}$, $R^{p7}$, $R^{p8}$, $R^{p9}$ and $R^{p10}$ include a methyl group, an ethyl group, a n-propyl group, an i-propyl group, an n-butyl group, an i-butyl group, a sec-butyl group, a t-butyl group, a n-pentyl group, an i-pentyl group, a t-pentyl group, a neo-pentyl group, and the like.

Examples of the structural unit (p) include a structural unit derived from a 1-alkyl-1-monocyclic cycloalkyl(meth)acrylate such as 1-ethyl-1-cyclopentyl (meth)acrylate; a structural unit derived from 2-alkyl-2-polycyclic cycloalkyl(meth)acrylate such as 2-i-propyl-2-adamantyl(meth)acrylate; and the like.

It is preferred that the polymer (P) further has, in addition to the structural unit (p), a structural unit that includes a lactone structure, a cyclic carbonate structure, a sultone structure, a structure having a phenolic hydroxyl group, or a combination thereof (hereinafter, may be also referred to as "structural unit (q)").

Examples of the structural unit (q) include a structural unit that includes, for example:

a lactone structure such as a norbornanelactone structure and a butyrolactone structure;

a cyclic carbonate structure such as an ethylene carbonate structure and a propylene carbonate structure;

a sultone structure such as a norbornane sultone structure and a propane sultone structure;

a structure having a phenolic hydroxyl group such as a structure derived from a (meth)acrylic acid ester having a hydroxyphenyl structure, a hydroxynaphthyl structure or the like, a hydroxystyrene structure, and an α-methylhydroxystyrene structure; or the like.

Moreover, the polymer (P) may have a structural unit other than the structural unit (p) and the structural unit (q). Examples of the other structural unit include a structural unit that includes a hydrocarbon group having 4 to 20 carbon atoms (hereinafter, may be also referred to as "structural unit (r)"), a structural unit that includes a polar group such as an alcoholic hydroxyl group (hereinafter, may be also referred to as "structural unit (s)"), and the like. Examples of the structural unit (r) include a structural unit derived from a (meth)acrylic acid ester having an alkyl group having 4 to 20 carbon atoms, and the like. Examples of the structural unit (s) include a structural unit derived from a (meth)acrylic acid hydroxy group-containing (cyclo)alkyl ester such as (meth)acrylic acid hydroxyadamantyl ester, and the like.

The proportion of the structural unit (p) with respect to the total structural units constituting the polymer (P) falls within a range of preferably 30 mol % to 60 mol %. When the proportion of the structural unit (p) contained falls within the above range, the resolution of the photoresist composition can be improved. When the proportion of the structural unit (p) is less than the lower limit, the pattern formability of the photoresist composition may be impaired. When the proportion of the structural unit (p) is greater than the upper limit, the thickness of the resist film after removal of the resist upper layer film may be extremely decreased.

The proportion of the structural unit (q) with respect to the total structural units constituting the polymer (P) falls within a range of preferably 20 mol % to 60 mol %. When the proportion of the structural unit (q) contained falls within the above range, the solubility of the resist film provided from the photoresist composition in a developer solution can be properly adjusted, while adhesiveness of the resist film to a substrate can be improved. When the proportion of the structural unit (q) contained is less than the lower limit, the adhesiveness of the photoresist composition to a substrate may be impaired. When the proportion of the structural unit (q) contained is greater than the upper limit, the pattern formability of the photoresist composition may be impaired.

The proportion of the other structural unit contained with respect to the total structural units constituting the polymer (P) is preferably no greater than 20 mol %, and more preferably no greater than 15 mol %.

The acid generating agent (Q) is a substance which generates an acid therefrom by irradiation with (exposure to) a radioactive ray and dissociates an acid-labile group protecting an acidic group (carboxy group or the like) of the polymer by an action of the generated acid to regenerate the acidic group.

Examples of the acid generating agent (Q) include an onium salt such as a sulfonium salt, a tetrahydrothiophenium salt, an iodonium salt, a phosphonium salt, a diazonium salt and a pyridinium salt, an N-sulfonyloxyimide compound, a halogen-containing compound, a diazo ketone compound, and the like.

Examples of the sulfonium salt include triphenylsulfonium nonafluoro-n-butanesulfonate, 4-cyclohexylphenyldiphenylsulfonium nonafluoro-n-butanesulfonate, 1-(4-n-butoxynaphthalen-1-yl)tetrahydrothiophenium nonafluoro-n-butanesulfonate, triphenylsulfonium 2-(bicyclo[2.2.1]hepta-2'-yl)-1,1,2,2-tetrafluoroethanesulfonate, 1-(4-n-butoxynaphthyl)tetrahydrothiophenium 2-(bicyclo[2.2.1]hepta-2'-yl)-1,1,2,2-tetrafluoroethanesulfonate, triphenylsulfonium 2-(bicyclo[2.2.1]hepta-2'-yl)-1,1-difluoroethanesulfonate, and the like.

In addition to the polymer (P) and the acid generating agent (Q), the photoresist composition may include other component such as (R) an acid diffusion control agent and a surfactant. Examples of the acid diffusion control agent (R) include amine compounds such as trioctylamine and triethanolamine; N-t-alkoxycarbonyl-containing amide compounds such as R-(+)-(t-butoxycarbonyl)-2-piperidinemethanol and N-t-butoxycarbonyl-4-hydroxypiperidine; photodegradable bases such as triphenylsulfonium 10-camphorsulfonate and triphenylsulfonium salicylate; and the like.

The photoresist composition is prepared, for example, by dissolving the polymer (P), the acid generating agent (Q), and the acid diffusion control agent (R) and the like as required in a solvent. The total solid content concentration of the photoresist composition is preferably 0.2% by mass to 20% by mass in light of its ease of coating. In addition, the photoresist composition is typically used after being filtered through a filter with a pore size of about 30 nm.

A coating method of the photoresist composition is exemplified by conventionally well-known coating methods such as spin-coating, cast coating, roll coating, and the like. After coating the photoresist composition on the substrate, the photoresist composition may be subjected to prebaking (PB) in order to evaporate the solvent.

Step (2)

In the step (2), a resist upper layer film is provided on the resist film using the composition for forming a resist upper layer film according to the embodiment of the present invention. A coating method of the composition for forming a resist upper layer film is exemplified by the same methods as those for photoresist composition in the step (1). In this step, it is preferred to conduct prebaking (PB) after coating the composition for forming a resist upper layer film. In the case of the exposure through a liquid immersion medium, when the resist upper layer film is provided on the resist film in this manner, a liquid immersion liquid and the resist film are not in direct contact with each other, whereby the impairment of lithography performances of the resist film caused by penetration of the liquid immersion liquid into the resist film, and contamination of a lens of a projection aligner caused by a component eluted from the resist film into the liquid immersion liquid are effectively inhibited. Moreover, in the case of exposure to the EUV and the like, outgassing from the resist film can be effectively inhibited by providing the resist upper layer film on the resist film.

It is preferred to bring a thickness of the resultant resist upper layer film as closer to an odd multiple of $\lambda/4m$ (in which, $\lambda$ is a wavelength of the radioactive ray; and m is a refractive index of the protective film) as possible. By setting the thickness of the resist upper layer film in this manner, the effect of inhibiting reflection on an upper interface of the resist film can be enhanced.

Step (3)

In the step (3), the resist film having the resist upper layer film provided thereon is exposed.

In the case where an exposure in the step (3) is carried out through a liquid immersion medium, a liquid which has a greater refractive index than air is typically used as the liquid immersion medium. Water is preferably used as the liquid immersion medium, and pure water is more preferably used. Herein, the pH of the liquid immersion liquid may be adjusted as required. In the presence of the liquid immersion medium, more specifically, in a state in which a space between the lens of the aligner and the resist upper layer film is filled with the liquid immersion medium, an exposure light is emitted from the aligner to expose the resist upper layer film and the photoresist film to the exposure light through a mask having a predetermined pattern.

The exposure light used for the exposure in the step (3) may be appropriately selected in accordance with the type of the photoresist film and/or the resist upper layer film, and is exemplified by visible light rays; ultraviolet rays such as a g-line and an i-line; far ultraviolet rays such as an excimer laser beam; X-rays such as synchrotron radioactive rays; an EUV (13.5 nm); charged particle rays such as electron beams; and the like. Among these, a far ultraviolet ray, an EUV and an electron beam are preferred, an ArF excimer laser beam (wavelength: 193 nm), a KrF excimer laser beam (wavelength: 248 nm), an EUV and an electron beam are preferred, and an ArF excimer laser beam is more preferred. Moreover, the emission condition of the exposure light such as, for example, an exposure dose may be appropriately selected in accordance with the blend composition of the photoresist composition and/or the composition for forming a resist upper layer film, the type of an additive contained therein, and the like.

In order to improve resolution, pattern configuration, developability and the like of the resultant resist pattern, post exposure baking (PEB) is preferably carried out after the exposure. The PEB temperature may be appropriately selected in accordance with the type of the photoresist composition and/or the composition for forming a resist upper layer film employed, and the like, but is typically 30° C. to 200° C., and preferably 50° C. to 150° C. The PEB time is typically 5 sec to 600 sec, and preferably 10 sec to 300 sec.

Step (4)

In the step (4), the resist film exposed as described above is developed. A desired resist pattern can be thereby obtained. According to the resist pattern-forming method, since the resist upper layer film is provided from the composition for forming a resist upper layer film according to the embodiment of the present invention, the resist upper layer film can be readily removed by a developer solution during the development, or by a washing liquid during washing if the washing is carried out after the development. This means that a separate peeling step for removing the resist upper layer film is not required.

For the development with an alkali, the developer solution is preferably an aqueous alkaline solution prepared by dissolving at least one of alkaline compounds such as sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, a tetraalkylammonium hydroxide (for example, tetramethylammonium hydroxide (TMAH), tetraethylammonium hydroxide and the like), pyrrole, piperidine, choline, 1,8-diazabicyclo-[5.4.0]-7-undecene, 1,5-diazabicyclo-[4.3.0]-5-nonane is preferred. Among these, an aqueous solution of the tetraalkylammonium hydroxide is more preferred.

An appropriate amount of a water soluble organic solvent such as an alcohol such as methanol and ethanol as well as a surfactant may be added to the developer solution. It is to be noted that in the case of the development with an alkaline aqueous solution, washing with water is preferably carried out after the development, and drying may be carried out after washing with water.

Moreover, a liquid containing an organic solvent may be used as the developer solution. Examples of such a developer solution include the solvents exemplified as the solvent (B) contained in the aforementioned composition for forming a resist upper layer film, and the like. Among these, an ester solvent, a ketone solvent and an ether solvent are preferred, and butyl acetate, methyl isoamyl ketone and anisole are more preferred. It is to be noted that in the case of the development with the organic solvent, washing with an organic solvent such as an alcohol solvent may be carried out after the development, and drying may be carried out after the washing.

EXAMPLES

Hereinafter, the embodiments of the present invention will be explained in more detail by way of Examples, but the present invention is not in any way limited by Examples. Measuring methods for various types of physical properties are shown below.

$^1$H-NMR, $^{13}$C-NMR and $^{19}$F-NMR analyses $^1$H-NMR, $^{13}$C-NMR and $^{19}$F-NMR analyses were carried out using a nuclear magnetic resonance apparatus (JNM-ECX400, manufactured by JEOL, Ltd.), CDCl$_3$ as a measurement solvent, and tetramethylsilane (TMS) as an internal standard.

Determination of Mw and Mn

Mw and Mn of the polymer were determined by gel permeation chromatography (GPC) under the following conditions:
GPC columns: G2000HXL×2, G3000HXL×1, G4000HXL×1 (manufactured by Tosoh Corporation)
elution solvent: tetrahydrofuran
flow rate: 1.0 mL/min
column temperature: 40° C.
standard substance: mono-disperse polystyrene
detector: differential refractometer Production of Compound Example 1

Into a 1 L three-neck reactor which was equipped with a dropping funnel and a condenser and dried, were charged 120.9 g of 1,1,1-trifluoro-2-trifluoromethyl-2,4-butanediol, 62.9 g of triethylamine and 200 mL of dichloromethane, and cooled to 0° C. in an ice bath. Thereafter, 100.0 g of ethyl 2-(bromomethyl)acrylate was added dropwise over 30 min. After the dropwise addition, the mixture was stirred at room temperature for 3 hours. Thereafter, precipitates were removed by filtration, and then 200 mL of 1 N hydrochloric acid was added to the resultant filtrate to stop the reaction. The resultant organic layer was washed sequentially with water and a saturated aqueous sodium chloride solution. Thereafter, the organic layer was dried over anhydrous magnesium sulfate and then concentrated in vacuo. Thereafter, purification was carried out through vacuum distillation to obtain 137.8 g (yield 82%) of a compound represented by the following formula (S-1).

$^1$H-NMR data of the product are shown below:
$^1$H-NMR (CDCl$_3$) δ: 1.31 (t, 3H), 2.27-2.30 (m, 2H), 3.89-3.91 (m, 2H), 4.22-4.28 (m, 4H), 5.81 (s, 1H), 6.37 (s, 1H)

Moreover, the resultant compound (S-1) was reacted with acetyl chloride in a dichloromethane solvent in the presence of triethylamine to obtain a compound represented by the following formula (S-7). "Ac" in the following formula (S-7) represents an acetyl group.

Example 2

A compound represented by the following formula (S-2) was obtained (124.1 g, yield 77%) in a similar manner to Example 1 except that 92.7 g of methyl 2-(bromomethyl) acrylate was used in place of 100.0 g of ethyl 2-(bromomethyl)acrylate used in Example 1.

$^1$H-NMR data of the product are shown below:
$^1$H-NMR (CDCl$_3$) δ: 2.29-2.32 (m, 3H), 3.90-3.93 (m, 2H), 4.23-4.30 (m, 4H), 5.83 (s, 1H), 6.35 (s, 1H)

Example 3

In a 1 L three-neck reactor which was equipped with a dropping funnel and a condenser and dried, 23.6 g of 1,1,1,3,3,3-hexafluoroisopropyl methacrylate, 55.4 g of N,N'-dibromo-N,N'-1,2-ethylene bis(2,5-dimethylbenzenesulfoneamide) and 24.2 g of dibenzoyl peroxide were dissolved in 1,000 mL of tetrachloroethane, and the solution was allowed to stir at room temperature for 1 hour. Thereafter, 1,000 mL of water was added to the reaction solution to stop the reaction. The resultant organic layer was washed with a saturated aqueous sodium chloride solution. Thereafter, the organic layer was dried over anhydrous magnesium sulfate and then concentrated in vacuo to obtain 22.0 g (yield 70%) of a precursor. Thereafter, into a 1 L three-neck reactor which was equipped with a dropping funnel and a condenser and dried were added 14.8 g of 1,1,1-trifluoro-2-trifluoromethyl-2,4-butanediol, 7.1 g of triethylamine and 200 mL of dichloromethane, and cooled to 0° C. in an ice bath. Thereafter, 22.0 g of the precursor was added dropwise over 30 min. After the dropwise addition, the mixture was allowed to stir at room temperature for 3 hours. Thereafter, precipitates were removed by filtration, and then 200 mL of 1 N hydrochloric acid was added to the resultant filtrate to stop the reaction. The resultant organic layer was washed sequentially with water and a saturated aqueous sodium chloride solution. Thereafter, the organic layer was dried over anhydrous magnesium sulfate and then concentrated in vacuo. Thereafter, purification was carried out through vacuum distillation to obtain 25.0 g (yield 80%) of a compound represented by the following formula (S-3).

¹H-NMR data of the product are shown below:
¹H-NMR (CDCl₃) δ: 3.85 (s, 1H), 3.90-3.93 (m, 2H), 4.23-4.30 (m, 4H), 5.83 (s, 1H), 6.35 (s, 1H)

Example 4

A compound represented by the following formula (S-4) was obtained (20.6 g, yield 75%) in a similar manner to Example 1 except that 128.9 g of 1,1,1-trifluoro-2-trifluoromethyl-2,4-pentanediol was used in place of 120.9 g of 1,1,1-trifluoro-2-trifluoromethyl-2,4-butanediol used in Example 1.
¹H-NMR data of the product are shown below:
¹H-NMR (CDCl₃) δ: 1.31 (t, 3H), 1.50 (t, 3H), 2.27-2.30 (m, 2H), 3.54 (q, 1H), 3.89-3.91 (m, 2H), 4.22-4.28 (m, 2H), 5.81 (s, 1H), 6.37 (s, 1H)

Example 5

A compound represented by the following formula (S-5) was obtained (27.4 g, yield 70%) in a similar manner to Example 3 except that 16.8 g of cyclohexyl methacrylate and 15.8 g of 1,1,1-trifluoro-2-trifluoromethyl-2,4-pentanediol in place of 23.6 g of 1,1,1,3,3,3-hexafluoroisopropyl methacrylate and 14.8 g of 1,1,1-trifluoro-2-trifluoromethyl-2,4-butanediol used in Example 3, respectively.
¹H-NMR data of the product are shown below:
¹H-NMR (CDCl₃) δ: 1.21-1.56 (m, 10H), 2.27-2.30 (m, 2H), 3.89-3.91 (m, 2H), 4.12-4.20 (m, 1H), 4.22-4.28 (m, 4H), 5.81 (s, 1H), 6.37 (s, 1H)

Synthesis of Polymer Component (A)

Monomers used for synthesis of the polymer (a) and the polymer (b) constituting the polymer component (A) are shown below.

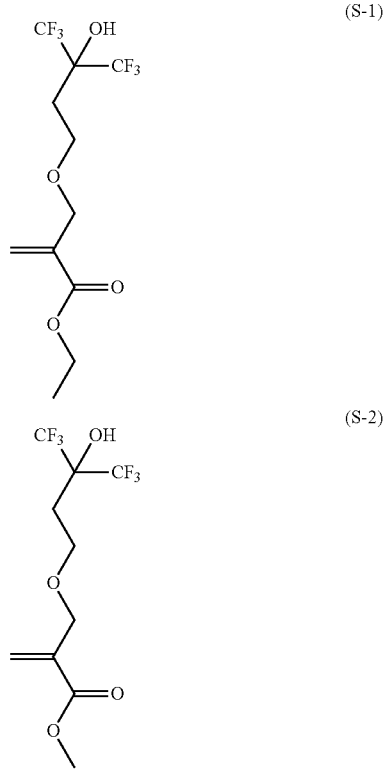

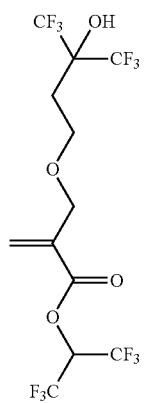

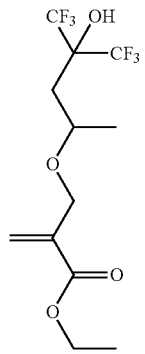

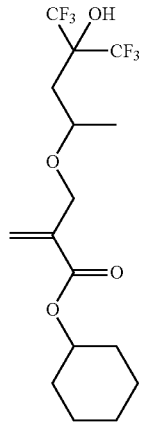

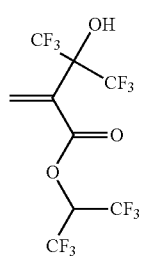

(S-7)
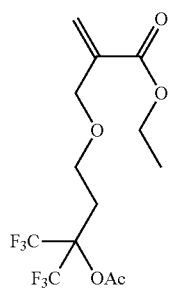
(M-1)
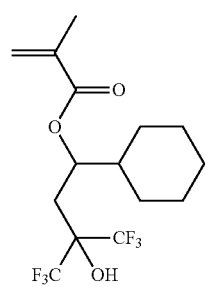
(M-2)
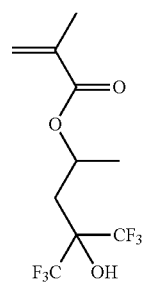
(M-3)
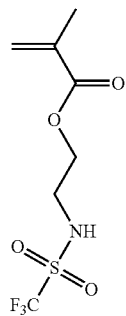
(M-4)
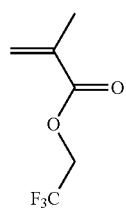
(M-5)
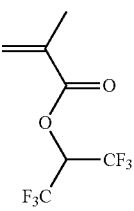
(M-6)
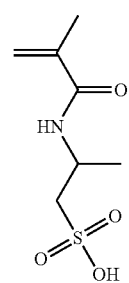
(M-7)
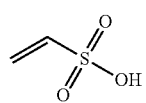
(M-8)
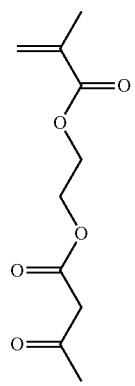
(M-9)
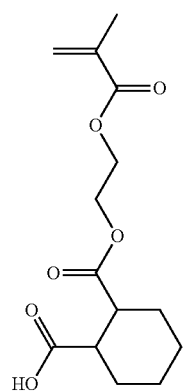
(M-10)
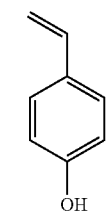

-continued

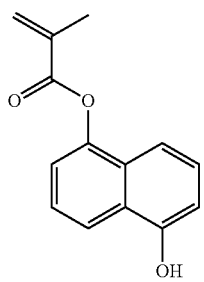

(M-11)

It is to be noted that the monomers (S-1) to (S-7) give the structural unit (I), the monomers (M-4) and (M-5) give the structural unit (II), the monomers (M-1) to (M-3) give the structural unit (III), the monomers (M-6) and (M-7) give the structural unit (IV), the monomers (M-8) and (M-9) give the structural unit (V), and the monomers (M-10) and (M-11) give the other structural unit, respectively.

Synthesis of Polymer (a)

Example 6

A polymerization initiator solution was prepared by dissolving 0.7 g of dimethyl 2,2-azobis(2-methylpropionate) as a polymerization initiator in 0.7 g of methyl ethyl ketone. Separately, into a 200 mL three-neck flask equipped with a thermometer and a dropping funnel were charged 9.4 g (50 mol %) of the monomer (S-1), 10.6 g (50 mol %) of the monomer (M-1) and 19.3 g of methyl ethyl ketone, and purging with nitrogen was executed for 30 min. After the purging with nitrogen, the mixture in the flask was heated with stirring with a magnetic stirrer such that a temperature of 75° C. was attained. Subsequently, the polymerization initiator solution prepared above was added dropwise over 5 min through the dropping funnel, and the mixture was incubated for 360 min. Thereafter, the mixture was cooled to no greater than 30° C. to obtain a polymerization reaction solution.

Next, the resultant polymerization reaction solution was concentrated to 44 g, and transferred to a separatory funnel. To this separatory funnel were charged 44 g of methanol and 220 g of n-hexane, and purification through liquid separation was carried out. After the separation, the underlayer liquid was recovered. To the recovered underlayer liquid was added 220 g of n-hexane, purification through liquid separation was carried out. After the separation, the underlayer liquid was recovered. The solvent component of the recovered underlayer liquid was replaced with 4-methyl-2-pentanol to obtain a solution containing a polymer (a-1). The polymer solution in an amount of 0.5 g was placed on an aluminum dish, and the aluminum dish was heated to 155° C. on a hot plate for 30 min to obtain a residue. The solid content concentration of the solution containing the polymer (a-1) was calculated from the mass of the remaining residue, and the value of the solid content concentration was used in a subsequent preparation of the composition for forming an upper layer film and in calculation of a yield. The resultant polymer (a-1) had an Mw of 10,100 and Mw/Mn of 2.1, and the yield thereof was 73%. Moreover, the proportions of the structural units derived from (S-1) and (M-1) were 51 mol % and 49 mol %, respectively. It is to be noted that the proportion (mol %) of each structural unit in the polymer was determined by $^1$H-NMR, $^{13}$C-NMR and $^{19}$F-NMR analyses.

Examples 7 to 20

The polymers (a-2) to (a-10) and (a-12) to (a-16) were each synthesized in a similar manner to Example 6 except that the type and amount of the monomer used were as specified in Table 1 below. It is to be noted that "-" in Table 1 indicates that the corresponding monomer was not used.

Synthesis Example 1

A monomer solution was prepared by dissolving 18.8 g (85 mol %) of the monomer (S-6) and 0.8 g of dimethyl 2,2-azobis(2-methylpropionate) as a polymerization initiator in 2.0 g of isopropanol. Separately, into a 200 mL three-neck flask equipped with a thermometer and a dropping funnel was charged 20 g of isopropanol, and purging with nitrogen was executed for 30 min. After the purging with nitrogen, the mixture in flask was heated with stirring with a magnetic stirrer such that a temperature of 80° C. was attained. Then, the monomer solution prepared above was added dropwise over 2 hours through the dropping funnel. After completing the dropwise addition, the reaction was allowed to proceed for another 1 hour, and then, 2 g of a solution of 1.2 g (15 mol %) of the monomer (M-7) in isopropanol was added dropwise over 30 min. Thereafter, the reaction was allowed to proceed for another 1 hour, and cooled to no greater than 30° C. to obtain a polymerization reaction solution.

The resultant polymerization reaction solution was concentrated to 44 g, and transferred to a separatory funnel. To the separatory funnel were charged 44 g of methanol and 264 g of n-hexane, and purification through separation was carried out. After the separation, the underlayer liquid was recovered. The underlayer liquid was transferred to the separatory funnel again. Thereafter, 264 g of n-hexane was charged into the separatory funnel to execute purification through separation, and after the separation, the underlayer liquid was recovered. The solvent component of the recovered underlayer liquid was replaced with 4-methyl-2-pentanol, and the total amount of the mixture was adjusted to 80 g. After the adjustment, 80 g of water was added to execute purification through separation, and after the separation, the upper layer liquid was recovered. The solvent component of the recovered upper layer liquid was replaced with 4-methyl-2-pentanol to obtain a solution containing the polymer (a-11). The resultant polymer (a-11) has an Mw of 9,990 and an Mw/Mn of 1.9, and the yield thereof was 78%. Moreover, the proportions of the structural units derived from (S-6) and (M-7) were 98 mol % and 2 mol %, respectively.

The proportions of the structural units, yield, values of Mw and Mw/Mn of each of the resultant polymer (a) are also shown in Table 1.

TABLE 1

| Polymer component (A) (polymer (a)) | | Monomer that gives structural unit (I) | | | Monomer that gives structural units (II) to (V) or other structural unit | | | Yield | Physical property | |
|---|---|---|---|---|---|---|---|---|---|---|
| | | type | amount used (mol %) | proportion (mol %) | type | amount used (mol %) | proportion (mol %) | (%) | Mw | Mw/Mn |
| Example 6 | a-1 | S-1 | 50 | 51 | M-1 | 50 | 49 | 73 | 10,100 | 2.1 |
| Example 7 | a-2 | S-1 | 50 | 46 | M-2 | 50 | 54 | 79 | 10,030 | 2.0 |
| Example 8 | a-3 | S-1 | 80 | 79 | M-3 | 20 | 21 | 82 | 9,920 | 1.8 |
| Example 9 | a-4 | S-1 | 50 | 47 | M-4 | 50 | 53 | 80 | 9,800 | 1.9 |
| Example 10 | a-5 | S-1 | 50 | 46 | M-5 | 50 | 54 | 79 | 10,030 | 2.0 |
| Example 11 | a-6 | S-1 | 100 | 100 | — | — | — | 83 | 10,200 | 2.1 |
| Example 12 | a-7 | S-2 | 60 | 60 | M-4 | 40 | 40 | 81 | 9,980 | 1.9 |
| Example 13 | a-8 | S-3 | 80 | 81 | M-5 | 20 | 19 | 77 | 9,100 | 2.1 |
| Example 14 | a-9 | S-4 | 50 | 51 | M-1 | 50 | 49 | 71 | 11,700 | 2.1 |
| Example 15 | a-10 | S-5 | 20 | 19 | M-1 | 80 | 81 | 81 | 10,040 | 2.2 |
| Example 16 | a-12 | S-1 | 75 | 76 | M-8 | 25 | 24 | 81 | 10,010 | 1.8 |
| Example 17 | a-13 | S-1 | 75 | 74 | M-9 | 25 | 26 | 79 | 10,090 | 1.8 |
| Example 18 | a-14 | S-1 | 25 | 25 | M-5 | 50 | 50 | 80 | 10,050 | 1.8 |
| | | S-7 | 25 | 25 | | | | | | |
| Example 19 | a-15 | S-2 | 85 | 85 | M-10 | 15 | 15 | 73 | 8,000 | 1.8 |
| Example 20 | a-16 | S-3 | 85 | 84 | M-11 | 15 | 16 | 75 | 8,500 | 1.8 |
| Synthesis Example 1 | a-11 | S-6 | 85 | 98 | M-7 | 15 | 2 | 78 | 9,990 | 1.9 |

Synthesis of Polymer (b)

Synthesis Examples 2, 3 and 5 to 7 (Synthesis of Polymers (b-1), (b-2) and (b-4) to (b-6))

The polymers (b-1), (b-2) and (b-4) to (b-6) were synthesized respectively in the same manner to Synthesis Example 1 except that the type and amount of the monomer used were as specified in Table 2 below.

Synthesis Example 4 (Synthesis of Polymer (b-3))

The polymer (b-3) was synthesized in the same manner to Example 6 except that the type and amount of the monomer used were as specified in Table 2 below.

The proportion of each structural unit, yield, and values of Mw and Mw/Mn of each of the polymer (b) thus obtained are also shown in Table 2.

TABLE 2

| Polymer (b) | Monomer that gives structural units (II) to (V) | | | Yield (%) | Physical property | |
|---|---|---|---|---|---|---|
| | type | amount used (mol %) | proportion (mol %) | | Mw | Mw/Mn |
| Synthesis Example 2 | b-1 | M-1 | 85 | 98 | 78 | 9,980 | 1.7 |
| | | M-7 | 15 | 2 | | | |
| Synthesis Example 3 | b-2 | M-2 | 85 | 98 | 80 | 9,910 | 1.6 |
| | | M-7 | 15 | 2 | | | |
| Synthesis Example 4 | b-3 | M-2 | 50 | 51 | 53 | 11,000 | 1.6 |
| | | M-5 | 50 | 49 | | | |
| Synthesis Example 5 | b-4 | M-3 | 95 | 95 | 81 | 10,200 | 1.7 |
| | | M-6 | 5 | 5 | | | |
| Synthesis Example 6 | b-5 | M-6 | 5 | 5 | 78 | 5,600 | 1.8 |
| | | M-9 | 95 | 95 | | | |
| Synthesis Example 7 | b-6 | M-2 | 60 | 69 | 76 | 5,300 | 1.8 |
| | | M-7 | 15 | 2 | | | |
| | | M-8 | 26 | 29 | | | |

Preparation of Composition for Forming Resist Upper Layer Film

Each of the solvent (B) used in the preparation of compositions for forming a resist upper layer film is shown below.
(B) Solvent
 B-1: 4-methyl-2-pentanol
 B-2: diisoamyl ether Preparation of Composition for Forming Resist Upper Layer Film for Liquid Immersion Lithography Example 21 (Preparation of Composition for Forming Resist Upper Layer Film (J-1))

Fifty parts by mass of (a-1) and 50 parts by mass of (b-1) as the polymer component (A) and 1,000 parts by mass of (B-1) and 4,000 parts by mass of (B-2) as the solvent (B) were blended to prepare a composition for forming a resist upper layer film (J-1).

Examples 22 to 39 and Comparative Examples 1 and 2 ( Preparation of Compositions for Forming Resist Upper Layer Film (J-2) to (J-19) and (CJ-1) and (CJ-2))

The compositions for forming a resist upper layer film (J-2) to (J-19) and (CJ-1) and (CJ-2) were prepared in the same manner to Example 17 except that the type and the amount of each component blended were as specified in Table 3 below.

Preparation of Photoresist Composition

A photoresist composition for forming a resist film was prepared according to the following procedure.

Synthesis of (P) Polymer for Photoresist Composition

Each of the monomer used for the synthesis of the polymer for photoresist composition (P) is shown below.

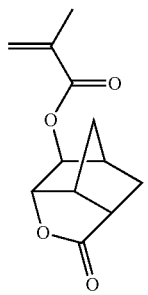
(r-1)

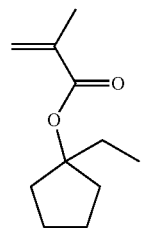
(r-2)

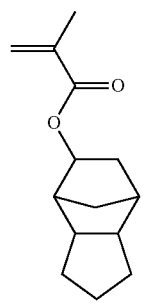
(r-3)

Synthesis Example 8

A monomer solution was prepared by dissolving 53.93 g (50 mol %) of the compound (r-1), 35.38 g (40 mol %) of the compound (r-2), and 10.69 g (10 mol %) of the compound (r-3) in 200 g of 2-butanone, and further dissolving 5.58 g of dimethyl 2,2'-azobis(2-methylpropionate) therein. Moreover, a 500 mL three-neck flask into which 100 g of 2-butanone was charged was purged with nitrogen for 30 min. After the purging with nitrogen, the reaction vessel was heated to 80° C. with stirring, and then the monomer solution prepared above was added thereto dropwise over 3 hours through a dropping funnel. The time of the start of the dropwise addition was regarded as the time of the start of the polymerization reaction, and the polymerization reaction was allowed to proceed for 6 hours. After completing the polymerization, the polymerization reaction solution was water-cooled to no greater than 30° C. and charged into 2,000 g of methanol, and a white powder deposited was filtered off. The filtered white powder was washed twice with 400 g of methanol (each) in a slurry state, filtered, and dried at 50° C. for 17 hours to obtain a polymer (P-1) as a white powder (74 g, yield 74%). The polymer (P-1) has an Mw of 6,900 and an Mw/Mn of 1.70. Moreover, the result of $^{13}$C-NMR analysis indicated that the proportion of each structural unit derived from (r-1):(r-2):(r-3) was 53.0:37.2:9.8 (mol %), respectively.

Preparation of Photoresist Composition (α)

(Q) an acid generating agent, (R) an acid diffusion control agent and (S) a solvent used in the preparation of the photoresist composition (α) are shown below.
Acid Generating Agent (Q)
  Q-1: triphenylsulfonium nonafluoro-n-butanesulfonate
  Q-2: 1-(4-n-butoxynaphthalen-1-yl)tetrahydrothiophenium nonafluoro-n-butanesulfonate
Acid Diffusion Control Agent (R)
  R-1: R-(+)-(t-butoxycarbonyl)-2-piperidinemethanol
Solvent (S)
  S-1: propylene glycol monomethyl ether acetate
  S-2: cyclohexanone
  S-3: γ-butyrolactone Preparation Example 1

The photoresist composition (α) was prepared by mixing 100 parts by mass of (P-1) as the polymer (P), 1.5 parts by mass of (Q-1) and 6 parts by mass of (Q-2) as the acid generating agent (Q), and 0.65 parts by mass of (R-1) as the acid diffusion control agent (R), adding 2,900 parts by mass of (S-1), 1,250 parts by mass of (S-2) and 100 parts by mass of (S-3) as the solvent (S) to the mixture to give the total solid content concentration of 5% by mass, and filtering the mixture through a filter with a pore size of 30 nm.
Evaluations Various types of evaluations described hereinafter were made for the compositions for forming a resist upper layer film obtained in the above Examples. The evaluation results are also shown in Table 3 described later.
Composition Stability Evaluation was made on the presence or absence of opacification over time of the compositions for forming a resist upper layer film.

After the composition for forming a resist upper layer film was stirred for 30 min, the presence or absence of opacification was visually determined.

The composition stability was determined to be "A" in the case of the absence of the opacification, and to be "B" in the case of the presence of the opacification.
Upper Layer Film Removability Evaluation was made on removability of a resist upper layer film with an alkaline developer solution.

A resist upper layer film with a film thickness of 90 nm was provided on an 8-inch silicon wafer by spin-coating a composition for forming a resist upper layer film on the 8-inch silicon wafer with a coater/developer (CLEAN TRACK ACT8, manufactured by Tokyo Electron Limited), followed by subjecting the same to prebaking (PB) at 90° C. for 60 sec. The film thickness was measured using a film thickness measurement system (Lambda Ace VM90, manufactured by Dainippon Screen Mfg. Co., Ltd.). The resist upper layer film was subjected to puddle development for 60 sec in the coater/developer using a 2.38% by mass aqueous TMAH solution as a developer solution, and spin-dried by spinning off the aqueous TMAH solution, and thereafter the surface of the wafer was observed. The removability of the upper layer film was evaluated to be "A" in the case where no residue was found, and to be "B" in the case where any residue was found.

Receding Contact Angle

A receding contact angle of water on a surface of a resist upper layer film was measured.

A resist upper layer film with a film thickness of 30 nm was provided on an 8-inch silicon wafer by spin-coating a composition for forming a resist upper layer film on the 8-inch silicon wafer, followed by subjecting the same to PB on a hot plate at 90° C. for 60 sec. Thereafter, a receding contact angle was measured quickly with a contact angle meter (DSA-10, manufactured by KRUS) in an environment involving a room temperature of 23° C., a humidity of 45%, and an ordinary pressure in accordance with the following procedure.

First, the position of a wafer stage of the contact angle meter was adjusted, and the wafer was placed on the adjusted stage. Next, water was injected into a needle, and the position of the needle was fine-tuned to an initial position which allowed a bead of water to be formed on the wafer placed as above. Thereafter, water was discharged from the needle to form a 25 μL bead of water on the wafer, the needle was once retracted from the bead of water, and the position of the needle was lowered to the initial position such that a tip of the needle was positioned in the bead of water. Subsequently, the water was aspirated for 90 sec with the needle at a rate of 10 μL/min, during which a contact angle was concurrently measured once per second, 90 times in total. Of the measurement values, contact angle measurements acquired for 20 sec after the time point when the measurement of the contact angle became stable were averaged to obtain a reading of the receding contact angle (unit: degree (°)). The measurements of the receding contact angle are shown in Table 3 shown later.

Elution Amount

Evaluation was made on the elution amount of a resist film component from a resist film that was provided with a resist upper layer film.

A silicone rubber sheet (manufactured by Kureha Elastomer Co., Ltd; a square sheet having a side length of 30 cm, with a thickness of 1.0 mm) with its central part being hollowed out in a circular shape with a diameter of 11.3 cm was mounted on the central part of an 8-inch silicon wafer that had undergone a treatment with hexamethyldisilazane (HMDS) at 100° C. for 60 sec in the coater/developer. Next, the hollowed central part of the silicone rubber was filled with 10 mL of ultrapure water using a 10 mL transfer pipet.

Separately from the silicon wafer, an 8-inch silicon wafer having an underlayer antireflective film, a resist film and a resist upper layer film provided was prepared, and this 8-inch silicon wafer was mounted on the silicone rubber such that the resist upper layer film was positioned on the silicone rubber sheet side, in other words, such that the resist upper layer film was in contact with the ultrapure water while keeping the ultrapure water from running out.

Note that the silicon wafer having an underlayer antireflective film, a resist film and a resist upper layer film provided was obtained by: spin-coating a composition for forming an underlayer antireflective film (ARC29A, manufactured by Brewer Science) on the 8-inch silicon wafer with the coater/developer to provide an underlayer antireflective film with a film thickness of 77 nm; then spin-coating the photoresist composition (α) on the underlayer antireflective film with the coater/developer and subjecting the same to baking at 115° C. for 60 sec to provide a resist film having a film thickness of 205 nm; and thereafter coating a composition for forming a resist upper layer film on the resist film and subjecting the same to PB at 90° C. for 60 sec to provide a resist upper layer film having a film thickness of 30 nm.

After the resist upper layer film was mounted, the state was maintained for 10 sec. Thereafter, the mounted 8-inch silicon wafer was removed and the ultrapure water was recovered with a glass syringe, and the recovered ultrapure water was designated as a sample for analysis. The recovery rate of the ultrapure water after completion of the experiment was no less than 95%.

Next, peak intensity of the anion moiety of the acid generating agent in the ultrapure water obtained as above was measured using a liquid chromatograph-mass spectrometer (LC-MS) (LC unit: SERIES 1100 (manufactured by AGILENT), and MS unit: Mariner (manufactured by Perseptive Biosystems, Inc.)) under the following measurement conditions. In the measurement, peak intensity of 1 ppb, 10 ppb, and 100 ppb aqueous solutions of the acid generating agent used in the photoresist composition (α) was measured under the following measurement condition to generate a calibration curve, and the amount of the acid generating agent eluted was calculated from the peak intensity using the calibration curve. The amount of the acid diffusion control agent eluted was also measured in a similar manner. Evaluation of "S" was made in the case of the amount of these eluted components being no greater than $1.0\times10^{-12}$ mol/cm$^2$, evaluation of "A" was made in the case of the amount of these eluted components being greater than $1.0\times10^{-12}$ mol/cm$^2$ and no greater than $5.0\times10^{-12}$ mol/cm$^2$, and evaluation of "B" was made in the case of the amount of these eluted components being greater than $5.0\times10^{-12}$ mol/cm$^2$.

Measurement Conditions column employed: CAPCELL PAK MG (manufactured by Shiseido Company, Limited)×1 flow rate: 0.2 mL/min elution solvent: water/methanol (3/7) supplemented with 0.1% by mass of formic acid measurement temperature: 35° C.

Peel Resistance

Evaluation was made on difficulty of peeling of a resist upper layer film from a substrate.

An 8-inch silicon wafer that had not undergone a treatment with HMDS was used as a substrate. A coating film (resist upper layer film) with a film thickness of 30 nm was provided on the substrate by spin-coating a composition for forming a resist upper layer film on the substrate with the coater/developer, followed by subjecting the same to PB at 90° C. for 60 sec. Thereafter, the resist upper layer film was subjected to rinsing with pure water for 60 sec in the coater/developer, and dried by spinning off the pure water. Peel resistance was evaluated to be "B" if peeling of the resist upper layer film was visually found on the entire surface of the wafer after rinsing, to be "A" if peeling was visually found only in an edge portion, and to be "S" if no peeling was visually found.

Pattern Configuration

Evaluation was made on the excellence of a pattern configuration of a resist pattern formed from a resist film that was provided with a resist upper layer film.

An underlayer antireflective film with a film thickness of 77 nm was provided on an 8-inch silicon wafer substrate by coating a composition for forming an underlayer antireflective film (ARC29A, manufactured by Brewer Science) on the 8-inch silicon wafer substrate with the coater/developer. Then, a resist film with a film thickness of 205 nm was provided on the underlayer antireflective film by spin-coating the photoresist composition (α) on the underlayer antireflective film, followed by subjecting the same to PB at 115° C. for 60 sec, and then a resist upper layer film with a film thickness of 30 nm was provided on the resist film by coating a composition for forming a resist upper layer film on the resist film, followed by subjecting the same to PB at 90° C. for 60 sec.

Next, the resist film provided was exposed using an ArF excimer laser Immersion Scanner (S610C, manufactured by NIKON) through a mask pattern for forming a line-and-space pattern (1L/1S) having a line width of 90 nm. Next, the resist film was subjected to PEB at 115° C. for 60 sec, developed with a 2.38% by mass aqueous TMAH solution as a developer solution at 23° C. for 60 sec, washed with water, and dried to form a positive resist pattern. In this process, an exposure dose resulting in formation of a line-and-space pattern (1L/1S) having a line width of 90 nm was designated as optimum exposure dose.

The cross-sectional shape of the resist pattern formed at the optimum exposure dose was observed with a scanning electron microscope (S-4800, manufactured by Hitachi High-Technologies Corporation). A line width Lb in the middle portion along the altitude direction of the resist pattern and a line width La at the top of the film were determined, and an La/Lb value was calculated. In a case where the La/Lb value fell within a range of no less than 0.9 and no greater than 1.1, the resist pattern was evaluated to be "S" as being rectangular in terms of cross-sectional shape; in a case where the La/Lb value fell within a range of no less than 0.8 and less than 0.9 or a range of greater than 1.1 and no greater than 1.2, the resist pattern was evaluated to be "A" as being nearly rectangular in terms of cross-sectional shape; and in a case where the La/Lb value was less than 0.8 or greater than 1.2, the resist pattern was evaluated to be "B" as being in a shape other than a rectangle such as a T-top shape, a top-round shape or a tailing shape in terms of cross-sectional shape.

Blob Defect

The number of blob defects generated in a resist pattern obtained after development of a resist film having a resist upper layer film provided thereon was determined.

A 12-inch silicon wafer was prepared which had undergone a treatment with hexamethyldisilazane (HMDS) at 100° C. for 60 sec using a coater/developer (Lithius Pro-i, manufactured by Tokyo Electron Limited). A resist film with a film thickness of 100 nm was provided on the 12-inch silicon wafer by spin-coating the photoresist composition (α) on the 12-inch silicon wafer, followed by subjecting the same to PB on a hot plate at 100° C. for 60 sec. A resist upper layer film with a film thickness of 30 nm was provided on the resist film by spin-coating a composition for forming a resist upper layer film on the resist film, followed by subjecting the same to PB at 90° C. for 60 sec. Next, the resist film was exposed through a mask for forming a pattern with a 45 nm line/90 nm pitch, using an ArF Immersion Scanner (S610C, manufactured by NIKON) under the optical conditions involving NA of 1.30 and Crosspole. The 12-inch silicon wafer having the exposed resist film thereon was used for the evaluation of the blob defect.

In the evaluation of the blob defect, ultrapure water was first discharged for 60 sec from a rinsing nozzle of the coater/developer "Lithius Pro-i" onto the resist upper layer film provided on the 12-inch silicon wafer having the exposed resist film for evaluation thereon, and the resist upper layer film was spin-dried by spinning off the ultrapure water at 4,000 rpm for 15 sec. Next, puddle development was carried out for 30 sec with an LD nozzle of the "Lithius Pro-i" to remove the resist upper layer film. It is to be noted that in the puddle development, a 2.38% by mass aqueous TMAH solution was used as a developer solution. After the development, the number of the blob defects in an unexposed area was determined using a defect inspection apparatus (KLA2810, manufactured by KLA Tencor). Evaluation was made to be "S" in the case of the number of the detected blob defects being no greater than 200 per wafer, to be "A" in the case of the number of the detected blob defects being greater than 200 and no greater than 500 per wafer, and to be "B" in the case of the number of the detected blob defects being greater than 500 per wafer.

Bridge Defect

The number of bridge defects generated in a resist pattern obtained after development of a resist film having a resist upper layer film provided thereon was determined.

A coating film with a film thickness of 105 nm was provided on a 12-inch silicon wafer surface by spin-coating a composition for forming an underlayer antireflective film (ARC66, manufactured by Nissan Chemical Industries, Ltd.) on the 12-inch silicon wafer surface with a coater/developer (Lithius Pro-i, manufactured by Tokyo Electron Limited), followed by subjecting the same to PB. Next, a resist film with a film thickness of 100 nm was provided by spin-coating the photoresist composition (α) using the aforementioned "CLEAN TRACK ACT12", subjecting the same to PB at 100° C. for 60 sec, and cooling it at 23° C. for 30 sec. Thereafter, a resist upper layer film with a film thickness of 30 nm was provided on the resist film by spin-coating a composition for forming a resist upper layer film on the resist film, followed by subjecting the same to PB at 90° C. for 60 sec.

Next, the resist film was exposed through a mask for forming a pattern with a 45 nm line/90 nm pitch, using an ArF Immersion Scanner (S610C, manufactured by NIKON) under the optical conditions involving NA of 1.30 and Crosspole. Next, the resist film was subjected to PEB on a hot plate of the aforementioned "Lithius Pro-i" at 100° C. for 60 sec, cooled at 23° C. for 30 sec, subjected to puddle development for 10 sec with a 2.38% by mass aqueous TMAH solution as a developer solution in a GP nozzle of a development cup, and rinsed with ultrapure water. Thereafter, the resist film was spin-dried by spinning off the ultrapure water at 2,000 rpm for 15 sec to obtain a substrate having the resist pattern formed thereon. In this process, an exposure dose resulting in formation of the resist pattern with a 45 nm line/90 nm pitch was designated as optimum exposure dose. In the formation of the resist pattern at the optimum exposure dose, evaluation was made to be "S" in the case of the number of the bridge defects being no greater than 100 per wafer, to be "A" in the case of the number of the bridge defects being greater than 100 and no greater than 300 per wafer, and to be "B" in the case of the number of the bridge defects being greater than 300 per wafer.

TABLE 3

| Composition for resist upper layer film | Polymer component (A) | | | | Solvent (B) | | Composition stability | Evaluation results | | | | | | |
|---|---|---|---|---|---|---|---|---|---|---|---|---|---|---|
| | polymer (a) | | polymer (b) | | | | | upper layer film removability | receding contact angle (°) | elution amount | peel resistance | pattern configuration | blob defect | bridge defect |
| | type | amount blended (parts by mass) | type | amount blended (parts by mass) | type | amount blended (parts by mass) | | | | | | | | |
| Example 21 | J-1 | a-1 | 50 | b-1 | 50 | B-1/B-2 | 1,000/4,000 | A | A | 77 | A | A | S | A | A |
| Example 22 | J-2 | a-1 | 50 | b-2 | 50 | B-1/B-2 | 1,000/4,000 | A | A | 76 | A | A | S | A | A |
| Example 23 | J-3 | a-1 | 80 | b-3 | 20 | B-1/B-2 | 1,000/4,000 | A | A | 81 | S | A | S | A | A |
| Example 24 | J-4 | a-1 | 55 | b-1/b-4 | 40/5 | B-1/B-2 | 1,000/4,000 | A | A | 75 | A | A | A | S | S |
| Example 25 | J-5 | a-1 | 50 | b-1/b-5 | 40/10 | B-1/B-2 | 4,000/1,000 | A | A | 75 | A | S | A | S | S |
| Example 26 | J-6 | a-1 | 50 | b-1/b-6 | 40/10 | B-1/B-2 | 4,000/1,000 | A | A | 75 | A | S | A | S | S |
| Example 27 | J-7 | a-2 | 10 | b-1 | 90 | B-1/B-2 | 1,000/4,000 | A | A | 74 | A | A | A | A | A |
| Example 28 | J-8 | a-3 | 80 | b-1 | 20 | B-1/B-2 | 1,000/4,000 | A | A | 74 | A | A | A | A | A |
| Example 29 | J-9 | a-4 | 20 | b-1 | 80 | B-1/B-2 | 1,000/4,000 | A | A | 77 | A | A | S | A | A |
| Example 30 | J-10 | a-5 | 10 | b-1 | 90 | B-1/B-2 | 1,000/4,000 | A | A | 80 | S | A | S | A | A |
| Example 31 | J-11 | a-6 | 80 | b-3 | 20 | B-1/B-2 | 1,000/4,000 | A | A | 80 | A | A | S | A | A |
| Example 32 | J-12 | a-7 | 30 | b-1 | 70 | B-1/B-2 | 1,000/4,000 | A | A | 76 | A | A | A | A | A |
| Example 33 | J-13 | a-8 | 15 | b-1 | 85 | B-1/B-2 | 1,000/4,000 | A | A | 77 | A | A | S | A | A |
| Example 34 | J-14 | a-9 | 50 | b-1 | 50 | B-1/B-2 | 1,000/4,000 | A | A | 76 | A | A | S | A | A |
| Example 35 | J-15 | a-10 | 30 | b-1 | 70 | B-1/B-2 | 1,000/4,000 | A | A | 77 | A | A | S | A | A |
| Example 36 | J-16 | a-11 | 20 | b-1 | 80 | B-1/B-2 | 1,000/4,000 | A | A | 74 | A | S | A | S | S |
| Example 37 | J-17 | a-12 | 20 | b-1 | 80 | B-1/B-2 | 1,000/4,000 | A | A | 73 | A | S | A | S | S |
| Example 38 | J-18 | a-13 | 20 | b-1 | 80 | B-1/B-2 | 1,000/4,000 | A | A | 72 | A | S | A | S | S |
| Example 39 | J-19 | a-14 | 50 | b-1 | 50 | B-1/B-2 | 1,000/4,000 | A | A | 80 | A | A | S | S | S |
| Comparative Example 1 | CJ-1 | — | — | b-1 | 100 | B-1/B-2 | 1,000/4,000 | A | A | 71 | B | B | B | A | A |
| Comparative Example 2 | CJ-2 | — | — | b-3 | 100 | B-1/B-2 | 1,000/4,000 | A | B | 81 | A | B | A | B | B |

It has been found from the results shown in Table 3 that the composition for forming a resist upper layer film according to the embodiment of the present invention can provide a resist upper layer film exhibiting superior water repellency while maintaining performances such as the upper layer film removability and the peel resistance, and enables the occurrence of defects such as bridge defects and blob defects in the resist pattern to be inhibited.

Preparation of Composition for Forming Resist Upper Layer Film for Exposure to EUV and the Like Example 40 (Preparation of Composition for Forming Resist Upper Layer Film (J-20))

One hundred parts by mass of (a-15) as the polymer component (A) and 1,000 parts by mass of (B-1) and 4,000 parts by mass of (B-2) as the solvent (B) were blended to prepare a composition for forming a resist upper layer film (J-20).

Example 41 (Preparation of Composition for Forming Resist Upper Layer Film (J-21))

A composition for forming a resist upper layer film (J-21) was prepared in the same manner to Example 40 except that the type and the amount of each component blended were as specified in Table 4 shown later.

Preparation of Photoresist Composition

A photoresist composition for forming a resist film was prepared according to the following procedure.

Synthesis of Polymer for Photoresist Composition (P)

Monomers used in the synthesis of a polymer for photoresist composition (P) are shown below.

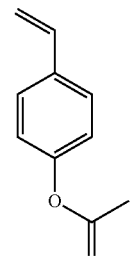

(r-4)

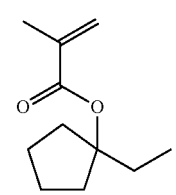

(r-5)

Synthesis Example 9

Fifty five g of a compound represented by the above formula (r-4), 45 g of a compound represented by the above formula (r-5), 3 g of AIBN and 1 g of t-dodecyl mercaptan were by dissolved in 150 g of propylene glycol monomethyl ether, and thereafter polymerization was allowed to proceed for 16 hours under a nitrogen atmosphere, while keeping the reaction temperature of 70° C. After the polymerization, the reaction solution was added dropwise to 1,000 g of n-hexane to purify a polymer through solidification. Then, to the polymer were added 150 g of propylene glycol monomethyl ether, then 150 g of methanol, 37 g of triethylamine and 7 g of water were further added, and a hydrolysis reaction was allowed to proceed for 8 hours with refluxing at the boiling point to achieve deacetylation of the structural unit derived from (r-4). After the reaction, the solvents and triethylamine were distilled off under vacuum, the resultant polymer was dissolved in 150 g of acetone, and then the solution thus obtained was added dropwise to 2,000 g of water to solidify the polymer. A white powder formed was filtered and dried at 50° C. overnight under a reduced pressure to obtain a polymer (P-2). The polymer (P-2) had an Mw of 6,000 and an Mw/Mn of 1.9. Moreover, the result of $^{13}$C-NMR analysis indicated that the proportions of the structural unit derived from p-hydroxystyrene: the structural unit derived from (r-5) were 50:50 (mol %).

Preparation of Photoresist Composition (β)

(Q) an acid generating agent, (R) an acid diffusion control agent and (S) a solvent used in the preparation of the photoresist composition (β) are shown below.
Acid Generating Agent (Q)
  Q-3: triphenylsulfonium n-nonafluorobutanesulfonate
Acid Diffusion Control Agent (R)
  R-2: triphenylsulfonium salicylate
Solvent (S)
  S-4: propylene glycol monomethyl ether acetate
  S-5: ethyl lactate Preparation Example 2

A photoresist composition (β) was prepared by mixing 100 parts by mass of (P-2) as the polymer (P), 27 parts by mass of (Q-3) as the acid generating agent (Q), and 2.6 parts by mass of (R-2) as the acid diffusion control agent (R), adding to the mixture 4,300 parts by mass of (S-4) and 1,900 parts by mass of (S-5) as the solvent (S), stirring the mixture, and filtering the mixture through a membrane filter with a pore size of 0.20 μm.
Evaluations Various types of evaluations described hereinafter were made for the compositions for forming a resist upper layer film obtained in the above Examples. The evaluation results are also shown in Table 4 shown later. In Comparative Example 3, the evaluation described below was made without providing a resist upper layer film ("-" in Table 4 indicates that a composition for forming a resist upper layer film was not used).
Bridge Defect The number of bridge defects generated in a resist pattern obtained after development of a resist film having a resist upper layer film provided thereon was determined.

A coating film with a film thickness of 20 nm was provided on a 12-inch silicon wafer surface by spin-coating a composition for forming an underlayer antireflective film (AL412, manufactured by Nissan Chemical Industries, Ltd.) on the 12-inch silicon wafer surface with a coater/developer (Lithius Pro-i, manufactured by Tokyo Electron Limited), followed by subjecting the same to PB. Next, a resist film with a film thickness of 50 nm was provided by spin-coating the photoresist composition (β) with the aforementioned "Lithius Pro-i", subjecting the same to PB at 130° C. for 60 sec, and cooling it at 23° C. for 30 sec. Thereafter, a liquid immersion resist upper layer film with a film thickness of 30 nm was provided on the resist film by spin-coating a composition for forming a resist upper layer film on the resist film, followed by subjecting the same to PB at 90° C. for 60 sec.

Patterning was carried out through irradiation with an electron beam using a simplified electron beam writer (manufactured by Hitachi, Ltd.; model HL800D; power: 50 KeV; electric current density: 5.0 ampere/cm$^2$). After the irradiation with the electron beam, PEB was carried out in the aforementioned "Lithius Pro-i" at 100° C. for 60 sec. Then, development by a puddle method was carried out in the aforementioned "Lithius Pro-i" at 23° C. for 1 min with a 2.38% by mass aqueous tetramethylammonium hydroxide solution, followed by washing with pure water, dried to form a resist pattern having an L/S of 1:1 and a pitch of 100 nm. The resist pattern thus formed was evaluated to be "A" in the case of no bridge defect being found, and to be "B" in the case of any bridge defect being found.
Local CDU A pattern-formed substrate was prepared in the same manner as the pattern-formed substrate used for the evaluation on the bridge defect described above. The width of the pattern was measured at arbitrary 100 points on the surface of the pattern-formed substrate using SEM (CG4000, manufactured by Hitachi High-Technologies Corporation), and a 3 Sigma value was calculated from a degree of distribution of the measurements of the width of the pattern and defined as local CDU. The local CDU was evaluated to be "A" in the case of the 3 Sigma value being no greater than 50, and to be "B" in the case of the 3 Sigma value being greater than 50 assuming that the 3 Sigma value calculated for Comparative Example 3 is 100. The symbol "-" for the local CDU of Comparative Example 3 in Table 4 indicates a reference for evaluation.
Inhibitory Effect on Outgassing A resist film with a film thickness of 50 nm was provide on a 12-inch silicon wafer by spin-coating the photoresist composition (β) prepared in Preparation Example 2 described above on the 12-inch silicon wafer in a coater/developer (Lithius Pro-i, manufactured by Tokyo Electron Limited), followed by subjecting the resist film to PB at 110° C. for 60 sec. Next, a resist upper layer film with a film thickness of 30 nm was provided by spin-coating a composition for forming a resist upper layer film on the silicon wafer having the resist film provided thereon, followed by subjecting the same to PB at 110° C. for 60 sec. An overall-exposure was carried out on the silicon wafer at an exposure dose of 15 mJ/cm$^2$ without a mask pattern using a KrF projection aligner (S203B, manufactured by Nikon Corporation) under the conventional optical conditions involving: NA, 0.68; Sigma, 0.75; and Conventional. An outgassing analysis was made for the wafer using a thermal desorption GC mass spectrometer (SWA-256, manufactured by GL Sciences, Inc.). Organic matter was desorbed from the wafer surface under a condition of 25° C. for 60 min, and the outgassed component desorbed was once collected in a collecting column. The organic matter was desorbed again from the collecting column by heating the collecting column at 200° C., and cooled in a thermal desorption cold trap injector with liquid nitrogen to allow for their contraction in volume. Thereafter, the collected gas component was introduced at once to a gas chromatograph (JNS-GCMATE GCMS SYSTEM, manufactured by JEOL, Ltd.) by rapidly heating to 230° C. to carry out the outgassing analysis. The inhibitory effect on outgassing of each composition for forming a resist upper layer film was evaluated in this way.

Analysis of Outgassing

The outgassing analysis was carried out for compounds represented by the following formulae (G-1), (G-2) and (G-3), and quantitative determination thereof was carried out based on the respective calibration curves created using the respective commercially available products. For each of (G-1), (G-2) and (G-3), a relative amount of each of (G-1), (G-2) and (G-3) were determined under the assumption that the amount of each of (G-1), (G-2) and (G-3) in Comparative Example 3 was 100, respectively. The inhibitory effect on outgassing was evaluated to be "A" in the case of all of the relative amount of (G-1), (G-2) and (G-3) being 0 to 60, and to be "B" in the case of the relative amount of at least one of (G-1), (G-2) and (G-3) being greater than 60.

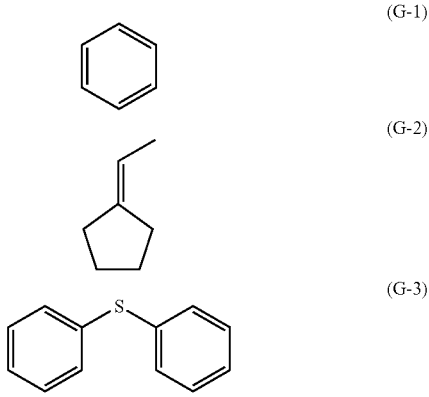

(G-1)

(G-2)

(G-3)

compound, the method for production of the compound and the polymer can be suitably applied to resist pattern formation through a liquid immersion lithography process that allows formation of a finer pattern.

Obviously, numerous modifications and variations of the present invention are possible in light of the above teachings. It is therefore to be understood that within the scope of the appended claims, the invention may be practiced otherwise than as specifically described herein.

The invention claimed is:

1. A composition comprising:
    a polymer component comprising a first polymer and optionally a second polymer which is other than the first polymer, wherein the first polymer has a structural unit represented by formula (1); and
    a solvent,

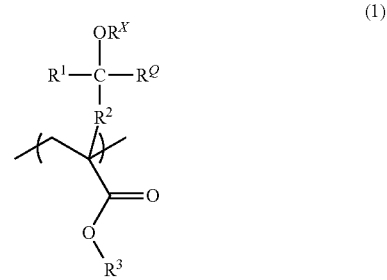

(1)

TABLE 4

| Composition for forming resist upper layer film | Polymer component (A) polymer (a) | | Solvent (B) | | Evaluation results | | |
|---|---|---|---|---|---|---|---|
| | type | amount blended (parts by mass) | type | amount blended (parts by mass) | bridge defect | local CDU | outgassing |
| Example 40 | J-20 | a-15 | 100 | B-1/B-2 | 1,000/4,000 | A | A | A |
| Example 41 | J-21 | a-16 | 100 | B-1/B-2 | 1,000/4,000 | A | A | A |
| Comparative Example 3 | — | — | — | — | — | B | — | B |

It has been found from the results shown in Table 4 that the composition for forming a resist upper layer film according to the embodiment of the present invention enables outgassing from the resist film to be effectively suppressed, a resist pattern having superior local CDU to be formed, and the occurrence of the bridge defects to be inhibited.

The composition for forming a resist upper layer film according to the embodiment of the present invention enables a resist upper layer film exhibiting superior water repellency to be provided and occurrence of defects such as bridge defects and blob defects in a resist pattern to be inhibited. Moreover, the compound according to the embodiment of the present invention can be suitably used as a monomer that gives a polymer contained in the composition for forming a resist upper layer film, and the method for production of the compound according to the embodiment of the present invention enables the compound to be produced conveniently and in high yield. The polymer of the embodiment of the present invention can be suitably used as a polymer component of the composition for forming a resist upper layer film. Therefore, the composition for forming a resist upper layer film, the wherein in the formula (1),
$R^1$ represents a hydrogen atom or a monovalent organic group having 1 to 20 carbon atoms;
$R^2$ represents a single bond or a divalent organic group having 1 to 20 carbon atoms;
$R^3$ represents a hydrogen atom or a monovalent organic group having 1 to 20 carbon atoms;
$R^Q$ represents a perfluoroalkyl group having 1 to 5 carbon atoms; and
$R^X$ represents a hydrogen atom or a monovalent base-labile group.

2. The composition according to claim 1, wherein the solvent comprises an ether solvent.

3. The composition according to claim 2, wherein the solvent further comprises an alcohol solvent.

4. The composition according to claim 1, wherein the divalent organic group having 1 to 20 carbon atoms represented by $R^2$ in the formula (1) is a divalent linear hydrocarbon group having 1 to 20 carbon atoms, a divalent alicyclic hydrocarbon group having 3 to 20 carbon atoms, or a group obtained by combining —O— with at least one of the divalent linear hydrocarbon group having 1 to 20 carbon atoms or the divalent alicyclic hydrocarbon group having 3 to 20 carbon atoms.

5. The composition according to claim 4, wherein the solvent comprises an ether solvent.

6. The composition according to claim 5, wherein the solvent further comprises an alcohol solvent.

7. The composition according to claim 1, wherein the monovalent organic group represented by $R^1$ and $R^3$ in the formula (1) is a monovalent hydrocarbon group, a monovalent hetero atom-containing group that includes between adjacent two carbon atoms of the monovalent hetero atom-containing group —O—, —CO—, —COO—, —NHCO—, —NH—SO$_2$—, —S— or a combination thereof, or a monovalent group derived from the monovalent hydrocarbon group or from the monovalent hetero atom-containing group by substituting a part or all of included hydrogen atoms with a fluorine atom, a hydroxy group, a carboxy group, an amino group, a cyano group or a combination thereof.

8. The composition according to claim 7, wherein the solvent comprises an ether solvent.

9. The composition according to claim 8, wherein the solvent further comprises an alcohol solvent.

10. The composition according to claim 1, wherein the polymer component further comprises, in the first polymer or the second polymer, a structural unit represented by formula (2),

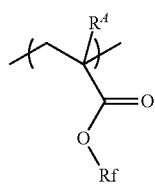

(2)

wherein in the formula (2), $R^4$ represents a hydrogen atom, a methyl group, a fluorine atom or a trifluoromethyl group; and Rf represents a fluorinated hydrocarbon group having 1 to 20 carbon atoms.

11. The composition according to claim 1, wherein the polymer component further comprises, in the first polymer or the second polymer, a structural unit that is a structural unit that includes a group represented by formula (3a), a structural unit that is other than the structural unit represented by the formula (1) and that includes a group represented by formula (3b), or a combination thereof,

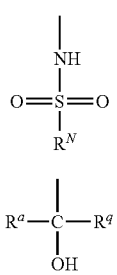

wherein in the formula (3a), $R^N$ represents a fluorinated hydrocarbon group having 1 to 20 carbon atoms, and in the formula (3b), $R^a$ represents a monovalent organic group having 1 to 20 carbon atoms; and $R^q$ represents a perfluoroalkyl group having 1 to 5 carbon atoms.

12. The composition according to claim 1, wherein the polymer component further comprises, in the first polymer or the second polymer, a structural unit that includes a sulfo group.

13. The composition according to claim 1, wherein the polymer component further comprises, in the first polymer or the second polymer, a structural unit that is a structural unit that includes a carboxy group, a structural unit that includes a group represented by formula (v), or a combination thereof,

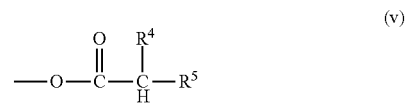

wherein in the formula (v),
$R^4$ represents a hydrogen atom, a halogen atom, a nitro group, an alkyl group, a monovalent alicyclic hydrocarbon group, an alkoxy group, an acyl group, an aralkyl group or an aryl group, wherein a part or all of hydrogen atoms included in the alkyl group, the alicyclic hydrocarbon group, the alkoxy group, the acyl group, the aralkyl group and the aryl group which are represented by $R^4$ are unsubstituted or substituted;
$R^5$ represents —C(=O)—$R^6$, —S(=O)$_2$—$R^7$, —$R^8$—CN or —$R^9$—NO$_2$;
$R^6$ and $R^7$ each independently represent a hydrogen atom, an alkyl group, a fluorinated alkyl group, a monovalent alicyclic hydrocarbon group, an alkoxy group, a cyano group, a cyanomethyl group, an aralkyl group or an aryl group, and
$R^4$ and $R^6$, or $R^4$ and $R^7$ optionally taken together represent a ring structure; and
$R^8$ and $R^9$ each independently represent a single bond, a methylene group or an alkylene group having 2 to 5 carbon atoms.

14. A resist pattern-forming method, comprising:
applying a photoresist composition directly or indirectly on a substrate to provide a resist film;
applying the composition according to claim 1 on the resist film to provide a resist upper layer film;
exposing the resist film having the resist upper layer film provided on the resist film; and
developing the exposed resist film.

15. The resist pattern-forming method according to claim 14, wherein the resist film is exposed through a liquid immersion medium.

16. The resist pattern-forming method according to claim 14, wherein the resist film is exposed using a far ultraviolet ray, an EUV or an electron beam.

17. A compound represented by formula (i),

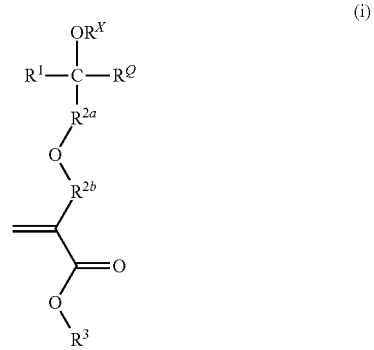

wherein in the formula (i),

R¹ represents a hydrogen atom or a monovalent organic group having 1 to 20 carbon atoms;

$R^{2a}$ represents a divalent linear hydrocarbon group having 1 to 16 carbon atoms, or a group obtained by combining —O— with the divalent linear hydrocarbon group;

$R^{2b}$ represents a divalent hydrocarbon group having 1 to 10 carbon atoms;

R³ represents a hydrogen atom or a monovalent organic group having 1 to 20 carbon atoms;

$R^Q$ represents a perfluoroalkyl group having 1 to 5 carbon atoms; and $R^X$ represents a hydrogen atom or a monovalent base-labile group.

18. A method for producing a compound, comprising:

reacting a dihydroxy compound represented by formula (i-a) with a haloalkylacrylic acid ester compound represented by formula (i-b) to produce a compound represented by formula (i'),

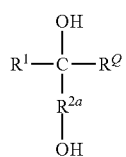

(i-a)

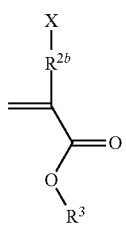

(i-b)

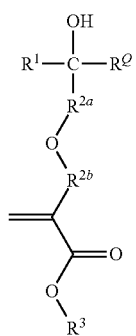

(i')

wherein in the formulae (i-a), (i-b) and (i'),

R¹ represents a hydrogen atom or a monovalent organic group having 1 to 20 carbon atoms;

$R^{2a}$ represents a divalent linear hydrocarbon group having 1 to 16 carbon atoms, or a group obtained by combining —O— with the divalent linear hydrocarbon group;

$R^{2b}$ represents a divalent hydrocarbon group having 1 to 10 carbon atoms;

R³ represents a hydrogen atom or a monovalent organic group having 1 to 20 carbon atoms;

$R^Q$ resents a perfluoroalkyl group having 1 to 5 carbon atoms; and

X represents a halogen atom.

19. A polymer comprising a structural unit represented by formula (1A),

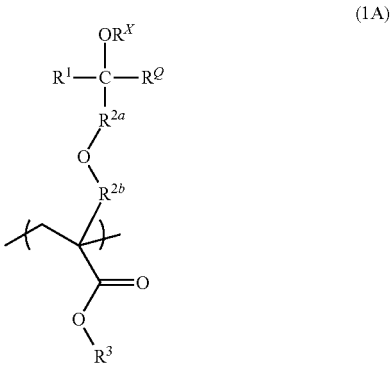

(1A)

wherein in the formula (1A), R¹ represents a hydrogen atom or a monovalent organic group having 1 to 20 carbon atoms;

$R^{2a}$ represents a divalent linear hydrocarbon group having 1 to 16 carbon atoms, or a group obtained by combining —O— with the divalent linear hydrocarbon group;

$R^{2b}$ represents a divalent hydrocarbon group having 1 to 10 carbon atoms;

R³ represents a hydrogen atom or a monovalent organic group having 1 to 20 carbon atoms;

$R^Q$ epresents a perfluoroalkyl group having 1 to 5 carbon atoms; and $R^X$ represents a hydrogen atom or a monovalent base-labile group.

* * * * *